US009658191B2

(12) United States Patent
Ohachi et al.

(10) Patent No.: US 9,658,191 B2
(45) Date of Patent: May 23, 2017

(54) ATOMIC FLUX MEASUREMENT DEVICE

(71) Applicants: THE DOSHISHA, Kyoto (JP); ARIOS INC., Tokyo (JP)

(72) Inventors: Tadashi Ohachi, Kyoto (JP); Motoi Wada, Kyoto (JP); Osamu Ariyada, Tokyo (JP); Nobuhiko Yamabe, Kyoto (JP)

(73) Assignee: THE DOSHISHA, Kyoto (JP)

( * ) Notice: Subject to any disclaimer, the term of this patent is extended or adjusted under 35 U.S.C. 154(b) by 1044 days.

(21) Appl. No.: 13/733,594

(22) Filed: Jan. 3, 2013

(65) Prior Publication Data

US 2013/0124124 A1 May 16, 2013

Related U.S. Application Data

(63) Continuation of application No. PCT/JP2011/065316, filed on Jul. 5, 2011.

(30) Foreign Application Priority Data

Jul. 5, 2010 (JP) .................................. 2010-152658
Dec. 24, 2010 (JP) .................................. 2010-287599

(51) Int. Cl.
*G01N 27/70* (2006.01)
*C23C 14/54* (2006.01)
(Continued)

(52) U.S. Cl.
CPC ........... *G01N 27/70* (2013.01); *C23C 14/543* (2013.01); *C30B 23/005* (2013.01); *G06F 17/00* (2013.01); *H05H 1/0081* (2013.01)

(58) Field of Classification Search
CPC ....... G06F 17/00; G01N 27/70; C23C 14/543; C30B 23/005
See application file for complete search history.

(56) References Cited

U.S. PATENT DOCUMENTS 1,421,720 A 7/1922 Roberts
3,628,139 A 12/1971 Huber
(Continued)

FOREIGN PATENT DOCUMENTS

JP 2009-146-755 A 7/2009
JP 2010-232496 A 10/2010

OTHER PUBLICATIONS

PCT International Search Report mailed Oct. 18, 2011 which is issued by JPO ISA in a related PCT International Application No. PCT/JP2011/065316 (2 pages).
(Continued)

*Primary Examiner* — Jeff Natalini
(74) *Attorney, Agent, or Firm* — Robert P. Michal, Esq.; Carter, DuLuca, Farrell & Schmidt, LLP

(57) ABSTRACT

An atomic flux measurement device for measuring the amount of dissociated atomic flux produced by discharge and emitted from a plasma generation cell into a vacuum camber. The atomic flux measurement device includes a counter electrode body including a pair of first and second sheet-like electrodes that are arranged substantially parallel to each other with a predetermined spacing between them, a direct-current power supply configured to maintain the first sheet-like electrode at a negative potential so that atoms attached to the inner surface of the sheet-like electrode undergo self-ionization and to apply a direct-current voltage between the first and second sheet-like electrodes so that a current flows between the first and second sheet-like electrodes, and a direct-current ammeter configured to measure a current flowing due to electrons emitted by the self-ionization of the dissociated atoms attached to the inner surface of the first sheet-like electrode.

6 Claims, 14 Drawing Sheets

(51) Int. Cl.
*C30B 23/00* (2006.01)
*H05H 1/00* (2006.01)
*G06F 17/00* (2006.01)

(56) References Cited

U.S. PATENT DOCUMENTS

| | | | | |
|---|---|---|---|---|
| 4,137,453 | A * | 1/1979 | Siegel | G01N 30/70 |
| | | | | 250/382 |
| 5,591,896 | A | 1/1997 | Lin | |
| 7,372,009 | B1 * | 5/2008 | Losee | G01T 3/08 |
| | | | | 250/200 |
| 7,645,996 | B2 | 1/2010 | Yang et al. | |
| 2003/0062262 | A1 * | 4/2003 | Mansouri | G01N 33/492 |
| | | | | 204/400 |
| 2007/0232985 | A1 * | 10/2007 | Sirkar | A61K 9/0009 |
| | | | | 604/20 |
| 2008/0032427 | A1 * | 2/2008 | Lee | H01J 37/32422 |
| | | | | 438/9 |
| 2009/0159791 | A1 * | 6/2009 | Wells | H01J 49/4265 |
| | | | | 250/282 |
| 2009/0224223 | A1 * | 9/2009 | Matsui | B82Y 10/00 |
| | | | | 257/2 |
| 2015/0155127 | A1 * | 6/2015 | Fink | H05H 3/06 |
| | | | | 250/427 |

OTHER PUBLICATIONS

Annex to the European Search Report on European Patent Application No. EP 11803562 dated Jul. 3, 2014 (2 pages).

* cited by examiner

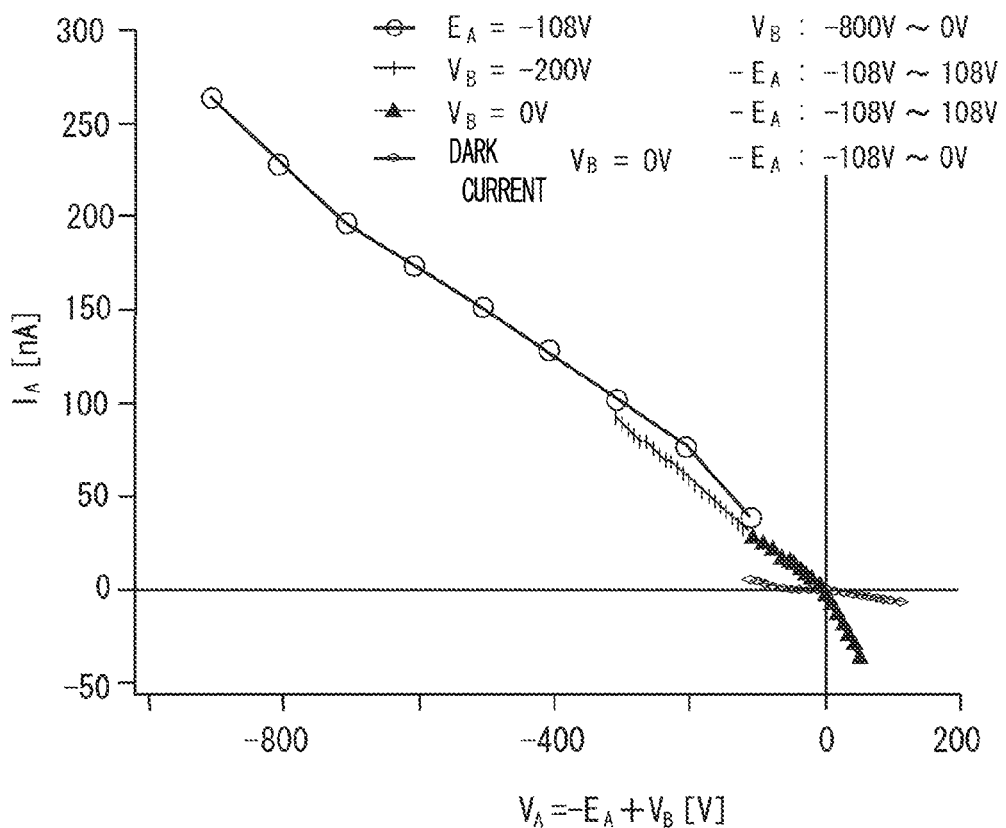
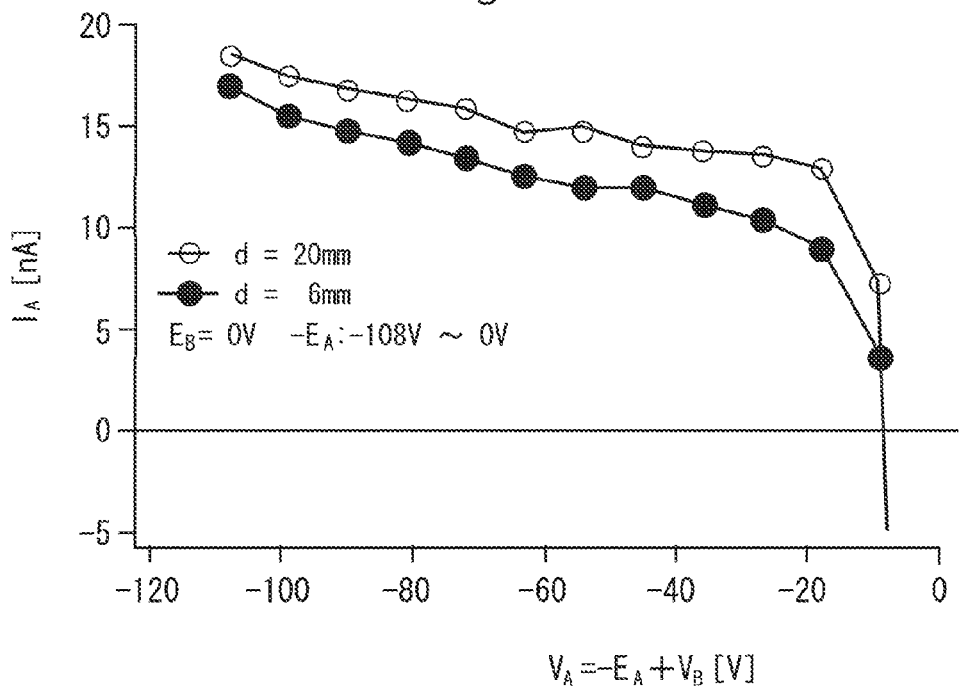

ATOMIC FLUX MEASUREMENT DEVICE

CROSS-REFERENCE TO RELATED APPLICATIONS

This is a Continuation of PCT International Application No. PCT/JP2011/065316 flied Jul. 5, 2011, which in turn claims priority from Japanese Patent Application Nos. 2010-152658 filed Jul. 5, 2010 and 2010-287599 filed Dec. 24, 2010, the entire disclosure of each of which is incorporated herein by reference.

TECHNICAL FIELD

The present invention relates to an atomic flux measurement device for measuring the amount of dissociated nitrogen atomic flux emitted from a plasma generation cell into a growth chamber.

BACKGROUND

A number of electronic devices using a group III nitride film, such as GaN, InGaN, InN or InAlN, on a substrate have been manufactured in recent years as electronic devices, such as blue light emitting diodes.

The device substrate is often formed of a sapphire film. The use of a single crystallin silicon substrate, which can be supplied at low cost and in large quantities, has been studied. The silicon substrate can also advantageously have a high thermal conductivity and therefore withstand high power operation compared to the sapphire substrate has.

When the group III nitride film is formed on a silicon substrate, it is necessary to form a buffer layer on the substrate in order to reduce lattice defects. The present inventors have previously proposed that a double buffer layer of $Si_3N_4$ and AlN are formed between the silicon substrate and the group III nitride film (see Patent Document 1).

A method for forming the double buffer layer between the Si substrate and the group III nitride film will be briefly explained with reference to FIGS. 17 to 19. FIG. 17 is a diagram schematically showing a configuration of an MBE (Molecular Beam Epitaxy) growth equipment that is used to form the buffer layers on the silicon substrate.

The MBE growth equipment 1 includes an RF (Radio Frequency) excitation cell 4 and a metal molecular beam cell 5 that are provided in a vacuum chamber (growth camber) 3, and an RF matching box 6, an RF power supply 7 and a personal computer (hereinafter referred to as a "PC") 8 that are provided outside the vacuum chamber 3. A counter electrode body 11 of an atomic flux measurement device 10 is provided in the vacuum chamber 3 in the vicinity of a substrate holder 31, while the main body of the atomic flux measurement device 10 is provided outside the vacuum chamber 3 and is connected to the PC 8 via a cable.

The vacuum chamber 3 is maintained at high vacuum ($10^{-4}$ to $10^{-8}$ Pa residual pressure) using a turbo molecular pump (not shown). A silicon substrate 2 that has already been subjected to the cleaning treatment is fixed to the substrate holder 31 and is heated to a predetermined temperature using a heater (not shown).

Although not shown, a shroud is provided on a sidewall surface of the vacuum chamber 3. The inside of the shroud is filled with liquid nitrogen. In the vacuum chamber 3, gas molecules are adsorbed by the wall surface when the gas molecules strike the sidewall, whereby a high degree of vacuum can be maintained.

The RF excitation cell 4 and the metal molecular beam cell 5 are provided in the wall of the vacuum chamber 3 to emit nitrogen atoms and metal molecules (e.g., Ga) toward the silicon substrate 2 held by the substrate holder 31. FIG. 18 shows a detailed structure of the RE excitation cell 4 that generates nitrogen gas plasma. Nitrogen gas supplied via a gas port 45 from a nitrogen gas cylinder (not shown) is supplied into a discharge chamber 42 of a hollow crucible 41. The amount of the nitrogen gas supplied is adjusted by a flow rate controller 46. An excitation coil 43 that also serves as a water cooling pipe is coaxially wound around the outer circumference of the crucible 41. By circulating cooling water W, the crucible 41 and the RF excitation cell 4 are cooled.

When high-frequency power is supplied to the excitation coil 43 from the RF power supply 7 via a terminal 63 of the RF matching box 6, the nitrogen gas in the discharge chamber 42 is excited into a plasma state so that a supersonic jet of an active species F of nitrogen is emitted through an orifice 44 provided in an output portion.

The metal molecular beam cell 5 melts a solid metal material (e.g., Ga) put in the crucible using a heater, and emits evaporated atoms toward the substrate 2 by opening and closing a shutter 9 attached to the output portion. Although the single metal molecular beam cell 5 is shown in FIG. 17, the vacuum chamber 3 typically includes a plurality of the metal molecular beam cells 5, the number of which depends on the number of metal molecules used.

The RF matching box 6 is provided to perform impedance matching between the RF power supply 7 and the plasma in the discharge chamber 42 so that the high-frequency power applied from the RF power supply 7 to the RF excitation cell 4 is smoothly supplied to the discharge chamber 42. The RF matching box 6 includes an automatic reactance adjustment circuit 61 and a variable reactance circuit 62.

In the above MBE growth equipment 1, the RF excitation cell 4 can be operated in two discharge modes. The first discharge mode is called an "HB discharge mode" in which a relatively high degree of high-frequency power (e.g., 500 W) is applied to the excitation coil 43 to excite nitrogen gas in the discharge chamber 42, whereby nitrogen plasma having a high brightness is obtained. In the HB discharge mode, as shown in spectrum line diagram of FIG. 19, emission of a flux (N+N*) of dissociated nitrogen atoms was observed including ground-state atoms N and excited atoms N* that are generated by dissociation of nitrogen molecules $N_2$, and excited nitrogen molecules $N_2^*$, nitrogen molecule ions $N_2^+$ and electrons.

A second discharge mode is called an "LB discharge mode" in which a relatively low degree of high-frequency power (e.g., 120 W) is applied to the excitation coil 43 to excite nitrogen gas in the discharge chamber 42, whereby nitrogen plasma having a low brightness is obtained. In the LB discharge mode, no flux (N+N*) of dissociated nitrogen atoms was contained in plasma emitted from the RF excitation cell 4, and emission of excited nitrogen molecules $N_2^*$, nitrogen molecule ions $N_2^+$ and electrons was observed.

The present inventors have extensively studied characteristics of the plasma generated in the HB discharge mode by conducting a variety of experiments. As a result, the present inventors have found that the excited atoms N* and the ground-state, atoms N contained in the plasma in the HB discharge mode are so-called metastable atoms, which have a thermodynamically relatively long life (of the order of milliseconds). On the other hand, the molecular ions $N_2^+$ and the electrons have the property that they quickly disappear due to recombination in the vacuum chamber. The present inventors also have found that the excited molecules $N_2^*$, the excited atoms $N^*$ and the ground-state atoms N contained in the plasma in the HB discharge mode are readily attached to a solid-phase interface, such as the substrate surface and the metal plate surface.

When a crystalline layer of GaN or AlGaN is grown on the silicon substrate, the substrate 2 is preferably directly irradiated with the high-energy excited atoms $N^*$ and ground-state atoms N emitted from the RF excitation cell 4. Such an irradiation technique is hereinafter referred to as "direct irradiation." In contrast to this, when a buffer layer is formed on the silicon substrate, the substrate is preferably indirectly irradiated with an appropriate amount of low-energy excited atoms $N^*$ and ground-state atoms N. Therefore, when a buffer layer is formed, as shown in FIG. 17, the HB-discharge-mode plasma emitted from the RF excitation cell 4 is caused to strike and rebound off a reflection plate 32 provided in the vacuum chamber 3 and, in addition, the shutter or the shroud in the RF excitation cell 4, at least once, so that the energy is reduced, before striking the surface of the substrate 2. Such an irradiation technique is hereinafter referred to as an "indirect irradiation."

Next, the step of forming the double buffer layer of $Si_3N_4$ and AlN between the silicon substrate and the group III nitride film using the above MBE growth equipment 1 will be briefly described. A treatment for cleaning the substrate surface is performed before the step of forming the $Si_3N_4$ buffer layer on the silicon substrate 2. The treatment is well known and therefore will not be described.

(1) The silicon substrate 2 that has been subjected to the cleaning treatment is fixed to the substrate holder 31 in the vacuum chamber 3, and is heated to a predetermined temperature using the heater.

(2) High-frequency power of, for example, 500 W having a frequency of 13.56 MHz is applied to the excitation coil 43 of the RF excitation cell 4 so that discharge occurs in the nitrogen gas in the HB discharge mode. The substrate is indirectly irradiated with a dissociated nitrogen atomic flux generated in the HB discharge mode, whereby a $\beta$-$Si_3N_4$ monocrystalline film is epitaxially grown by surface/interface reaction.

(3) The $Si_3N_4$ monocrystalline film is irradiated with an Al atomic flux corresponding to several atomic layers using an Al molecular beam cell, whereby an AlN monocrystalline film is epitaxially grown due to surface/interface reaction.

(4) The AlN monocrystalline film is directly irradiated with a dissociated nitrogen atomic flux and an excited nitrogen molecule flux that are generated in the HB discharge mode, and is also irradiated with an Al atomic flux using an Al molecular beam cell, whereby an AlN epitaxial layer is formed.

If a crystal of GaN or AlGaN is grown on the silicon substrate on which the double buffer layer have been formed by the above steps, a film having less lattice defects can be formed.

Incidentally, in order to control the growth operation of the MBE growth equipment 1 employing the RF excitation cell 4, it is necessary to monitor the amount of dissociated nitrogen atomic flux that strike the surface of the substrate 2. Conventionally, the amount of dissociated nitrogen atomic flux is measured using the Langmuir probe technique. However, the Langmuir probe technique is designed to measure a current flowing through a metal probe based on charged particles. As described above, particles (i.e., atoms and excited molecules) emitted from the RF excitation cell 4 are electrically neutral. Therefore, the amount of dissociated nitrogen atomic flux may not be correctly measured by the Langmuir probe technique.

The present inventors have previously developed an device for measuring the amount of dissociated nitrogen atomic flux (see Patent Document 2). This measurement device makes use of the phenomenon that when electrically neutral dissociated nitrogen atoms are attached to a probe electrode having a negative potential, the atoms emit electrons due to self ionization, whereby a current (hereinafter referred to as an "atomic current") flows. The value of the atomic current flowing through the probe electrode varies depending on the amount of the atomic flux in an atmosphere in which the probe electrode is placed. Therefore, the amount of the atomic flux can be determined by measuring the value of the current.

CITATION LIST

Patent Document

Patent Document 1: JP 2010-232496 A
Patent Document 2: JP 2009-146755 A.

SUMMARY OF INVENTION

Technical Problem

As described above, the value of the atomic current measured by the atomic flux measurement device varies depending on the amount of the atomic flux in an atmosphere in which the probe electrode is placed. Therefore, if the probe electrode is provided in the vicinity of the substrate 2, the amount of the atomic flux that strikes the substrate 2 can be determined as the value of the atomic current.

However, the value of the atomic current output from the probe electrode is low. The surface area of the probe electrode may be increased in order to increase the value of the atomic current. However, if the surface area of the electrode is increased, the size of the measurement device increases, and therefore, it becomes difficult to provide sufficient installation space in the vacuum chamber.

The present invention has been made with the above problems in mind. It is an object of the present invention to provide a low-cost and compact atomic flux measurement device capable of monitoring the flux amount of dissociated nitrogen atomic flux emitted from a plasma generation cell.

Solution to Problem

An atomic flux measurement device according to the present invention is one for measuring a amount of dissociated nitrogen atomic flux that are emitted from a plasma generation cell to a growth camber by discharge in a gas, including a counter electrode body including a pair of first and second sheet-like electrodes that face each other and are arranged substantially parallel to each other with a predetermined spacing between them, a first direct-current power supply configured to apply a direct-current voltage between the first and second sheet-like electrodes to cause the atoms attached to an inner surface of the first sheet-like electrode to undergo self-ionization so that a current flows between the first and second sheet-like electrodes, and a direct-current ammeter provided between the first and second sheet-like electrodes and configured to measure a value of the current flowing due to the self-ionization of the atoms attached to the inner surface of the first sheet-like electrode.

In the atomic flux measurement device of the present invention, the potential of the first sheet-like electrode is represented by $$V_A = -E_A + V_B$$

where $V_A$ is the potential of the first sheet-like electrode, $E_A$ is the electromotive force of the first direct-current power supply and has a value of zero or more, $V_B$ is the potential between the second sheet-like electrode and a ground terminal and is set to a value of zero or less by a second direct-current power supply.

The first sheet-like electrode is preferably formed of a metal plate, the first and second sheet-like electrodes are preferably formed of a metal mesh sheet, or the second sheet-like electrode is preferably formed of a metal mesh sheet. The first and second sheet-like electrodes of the counter electrode body may be rolled into a spiral with an insulating spacer being interposed between them. Alternatively, the first and second sheet-like electrodes may be formed of a plurality of plate-like metal mesh sheets having substantially the same shape, and the first and second sheet-like electrodes of the counter electrode body may be alternately stacked with a predetermined spacing.

The counter electrode body preferably includes a third sheet-like electrode that is formed of a metal mesh sheet and is provided on the side of the counter electrode body where the atomic flux enters, and a potential of the third sheet-like electrode is preferably set to be the same as a potential of the second sheet-like electrode. Alternatively, the counter electrode body preferably includes a fourth sheet-like electrode outside the first sheet-like electrode, on the side opposite to the side of the counter electrode body where the atomic flux enters, while being separated from the first sheet-like electrode by a predetermined spacing, and the fourth sheet-like electrode is preferably connected to the first sheet-like electrode.

The atomic flux measurement device of the present invention preferably further includes an A/D converter configured to convert a value of the atomic current measured by the direct-current ammeter into digital data, a memory configured to store the digital data output from the A/D converter, a display configured to display the digital data stored in the memory, and a controller configured to write and read data to and from the memory and control the operation of the display.

The atomic flux measurement device of the present invention preferably further includes a calculator configured to calculate the amount of flux based on the value of the atomic current measured by the direct-current ammeter. The calculator preferably reads out a table indicating a relationship between values of atomic currents and amounts of flux corresponding to the values of the atomic currents, the table being previously stored in the memory. The calculator preferably checks the value of the atomic current measured by the direct-current ammeter against the values of the atomic currents stored in the memory, to calculate the amount of flux corresponding to the value of the atomic current measured by the direct-current ammeter.

Advantageous Effects of Invention

The atomic flux measurement device of the present invention measures the amount of dissociated atomic flux emitted from an RF excitation cell based on a value of an atomic current flowing between a pair of sheet-like electrodes. In the atomic flux measurement device of the present invention, the sensitivity of measurement of the atomic current can be increased by applying an appropriate negative bias voltage to one of the electrodes. As a result, the atomic current can be measured using a relatively low-cost ammeter, and therefore, the cost of the measurement device can be reduced.

Also, the sheet-like electrodes may be formed of a metal mesh sheet and rolled or stacked, whereby the surface areas of the electrodes can be increased without an increase in the volume of the counter electrode body, resulting in a compact atomic flux measurement device having a high measurement sensitivity.

BRIEF DESCRIPTION OF DRAWINGS

FIG. 8 is a graph of voltage-current characteristics produced based on the result of measurement performed by the atomic flux measurement device of the first embodiment.

FIG. 9 is a graph of voltage-current characteristics produced based on the result of measurement performed by the atomic flux measurement device of the first embodiment.

DESCRIPTION OF EMBODIMENTS

Preferred embodiments of an atomic flux measurement device according to the present invention will be described hereinafter with reference to the accompanying drawings.

First Embodiment

<Configuration of Measurement Device>

Figure 1:
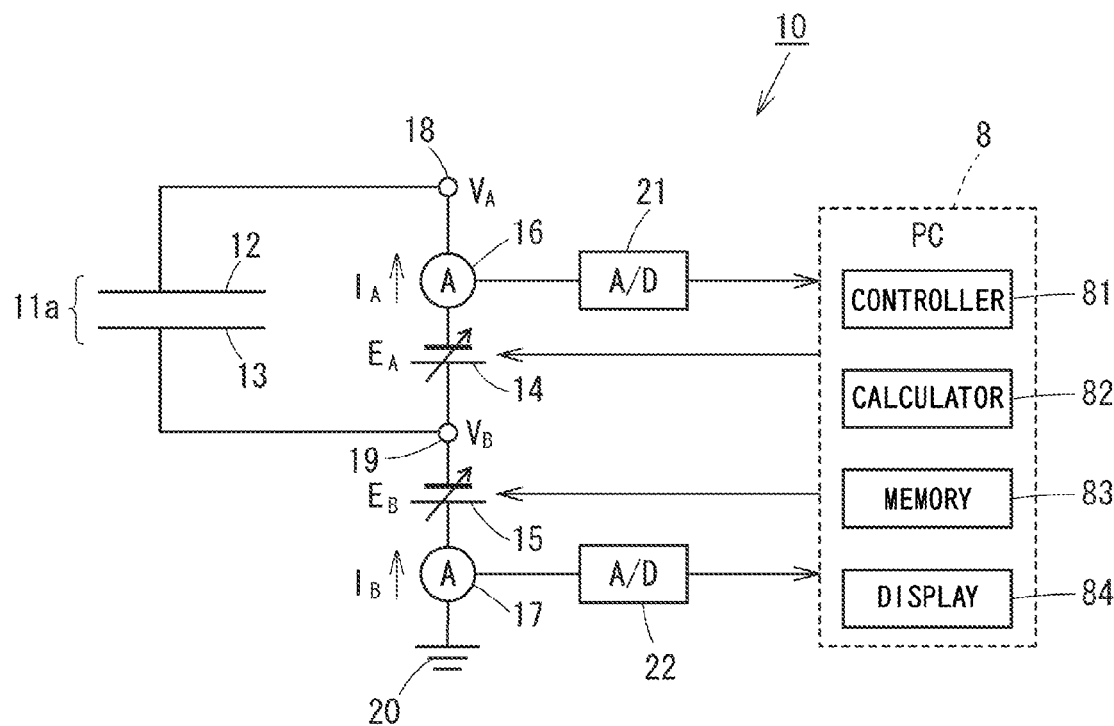
FIG. 1 is a diagram showing a basic configuration of an atomic flux measurement device according to a first embodiment of the present invention.

FIG. 1 shows a basic configuration of an atomic flux measurement device according to a first embodiment of the present invention. The atomic flux measurement device 1 includes a counter electrode body 11a, a first and a second direct-current power supply 14 and 15, a first and a second direct-current ammeter 16 and 17, a first and a second A/D converter 21 and 22 and a personal computer 8, which are used to measure the value of an atomic current occurring due to dissociated nitrogen atoms emitted from an RF excitation cell 4.

The counter electrode body 11a includes a first and a second sheet-like electrode 12 and 13 that are substantially parallel to each other with a predetermined spacing between them. The first sheet-like electrode 12 is connected to a first terminal 18, and the second sheet-like electrode 13 is connected to a second terminal 19. The first direct-current power supply 14 and the first direct-current ammeter 16 are connected together in series between the terminals 18 and 19. The second direct-current power supply 15 and the second direct-current ammeter 17 are connected together in series between the terminal 19 and a ground terminal (i.e., a terminal having a reference potential) 20.

<Specific Configuration of Counter Electrode Body>

Figure 2:
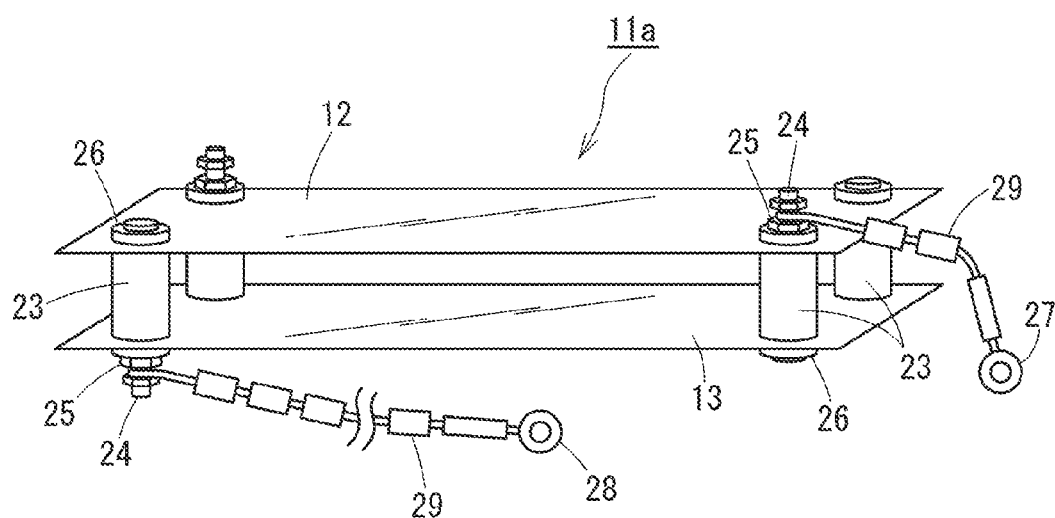
FIG. 2 is a diagram showing an example of a specific configuration of a counter electrode body in the first embodiment.

FIG. 2 shows an example of a specific configuration of the counter electrode body 11a. The sheet-like electrodes 12 and 13 are formed, for example, of a rectangular stainless steel sheet having a high boiling point, and have holes in the four corners. The pair of sheet-like electrodes 12 and 13 are separated from each other by a predetermined spacing, facing each other with insulating spacers 23 being interposed between them. The spacers 23 are fixed to the sheet-like electrodes 12 and 13 using nuts 25 and washers 26 by bolts 24 inserted into the holes provided at the four corners.

One end of a wire 27 is connected to one of the nuts 25 on the first sheet-like electrode 12, and one end of the wire 28 is connected to another of the nuts 25 on the second sheet-like electrode 13. The other end of the wire 27 is connected to the first terminal 18, and the other end of the wire 28 is connected to the second terminal 19. Outer circumference surfaces of the wires 27 and 28 are covered by alumina insulating tubes 29.

In this embodiment, the sheet-like electrodes 12 and 13 were formed of a rectangular flat plate of stainless steel (SUS) having a thickness of 0.5 mm and an area of 180 mm (L)×50 mm (W). An alumina bushing having a length of 6 mm is used as the spacer 23. A picoammeter (model 6487 manufactured by Keithley Instruments Inc. in the U.S.) was used as the first and second direct-current ammeters 16 and 17 of FIG. 1. A commercially available battery (accumulator) was used as the first direct-current power supply 14. An electronic direct-current power supply was used as the second direct-current power supply 15.

Also, in this embodiment, an IRFS-501 RF excited nitrogen source (trade name) manufactured by ARIOS INC. (in Tokyo, Japan) was used as the RF excitation cell 4, and was incorporated into a cell port of a VG80H-MBE growth equipment manufactured by VG SEMICON (in the U.K.). A combined product of the IRFS-501 RF excited nitrogen source, the RF matching box 6 and the RF power supply 7 is commercially available under the model name "IRFC-504" from ARIOS INC.

<Principle of Measurement of Amount of Flux>

Before describing the operation of the atomic flux measurement device 10, the principle of measurement of the amount of an atomic flux will be described with reference to FIGS. 1 and 3.

Figure 3A:
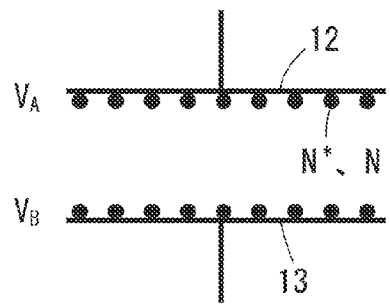
FIGS. 3(a) and 3(b) are diagrams for describing the principle of monitoring an atomic flux.

As described above, excited molecules $N_2^*$, excited atoms $N^*$ and ground-state atoms $N$ of nitrogen contained in plasma in the HB discharge mode have the properties that they are readily attached to a solid-phase interface, such as, for example, the substrate surface or the metal plate surface. Therefore, if the counter electrode body 11a is provided in a space in which a flux of dissociated nitrogen atoms emitted from the RF excitation cell 4 is present, as shown in FIG. 3(a) nitrogen molecules $N_2^*$, excited atoms $N^*$ and ground-state atoms $N$ are attached to the inner surfaces of the sheet-like electrodes 12 and 13 at a density corresponding to thermal equilibrium vapor pressure of the local space, as called indirect irradiation.

Figure 3B:
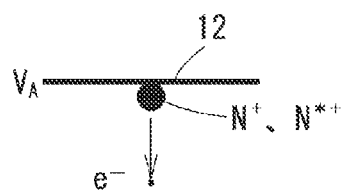

If an appropriate negative bias voltage, is applied to one (i.e. electrode 12) of the sheet-like electrodes 12 and 13 to which the dissociated nitrogen atoms are attached, excited atoms $N^*$ and ground-state atoms $N$ of the particles attached to the electrode surface undergo self-ionization, so that, as shown in FIG. 3(b), electrons $e^-$ are emitted from the sheet-like electrode 12 to which the negative bias voltage is applied, and reaches the sheet-like electrode 13 having a higher potential. As a result, an atomic current of electrons produced by self-ionization flows between the pair of the sheet-like electrodes 12 and 13.

In the circuit of FIG. 1, a potential (i.e. a potential of the first sheet-like electrode 12) $V_A$ of the terminal 18 corresponds to an electromotive force $E_A$ of the first direct-current power supply 14. On the other hand, a potential (i.e. a potential of the second sheet-like electrode 13) $V_B$ of the terminal 19 corresponds to an electromotive force $E_B$ of the second direct-current power supply 15, and is set to a negative potential $-E_B$ ($E_B \geq 0$). Specifically, the potential $V_A$ of the first sheet-like electrode 12 is set as follows:

$$V_A = -E_A + V_B < 0.$$

Note that the second direct-current power supply 15 may be removed, i.e., $E_B = 0$.

The negative potential $V_A$ ($=-E_A + V_B$) applied to the sheet-like electrode 12 causes self-ionization of the dissociated nitrogen atoms attached to the inner surface of the sheet-like electrode 12, so that an atomic current $I_A$ corresponding to the number (density) of the dissociated nitrogen atoms flows between the sheet-like electrodes 12 and 13. The value of the atomic current $I_A$ is measured by the first direct-current ammeter 16.

The atomic current $I_A$ is typically represented by $$I_A = -\gamma S F_N V_A + I_0 \tag{1}$$

where $\gamma$ is the self-ionization coefficient of the electrode surface, S is the effective electrode area, $F_N$ is the amount of dissociated nitrogen atomic flux on the electrode surface, and $I_0$ is the current flowing when the potential is zero. The sign "−" indicates that the current is formed of electrons emitted from the electrode having a negative potential.

As shown in Expression (1), the amount of dissociated nitrogen atomic flux and the atomic current $I_A$ have a linear relationship. Therefore, the amount of the atomic flux can be indirectly measured by measuring the atomic current $I_A$.

Figure 17:
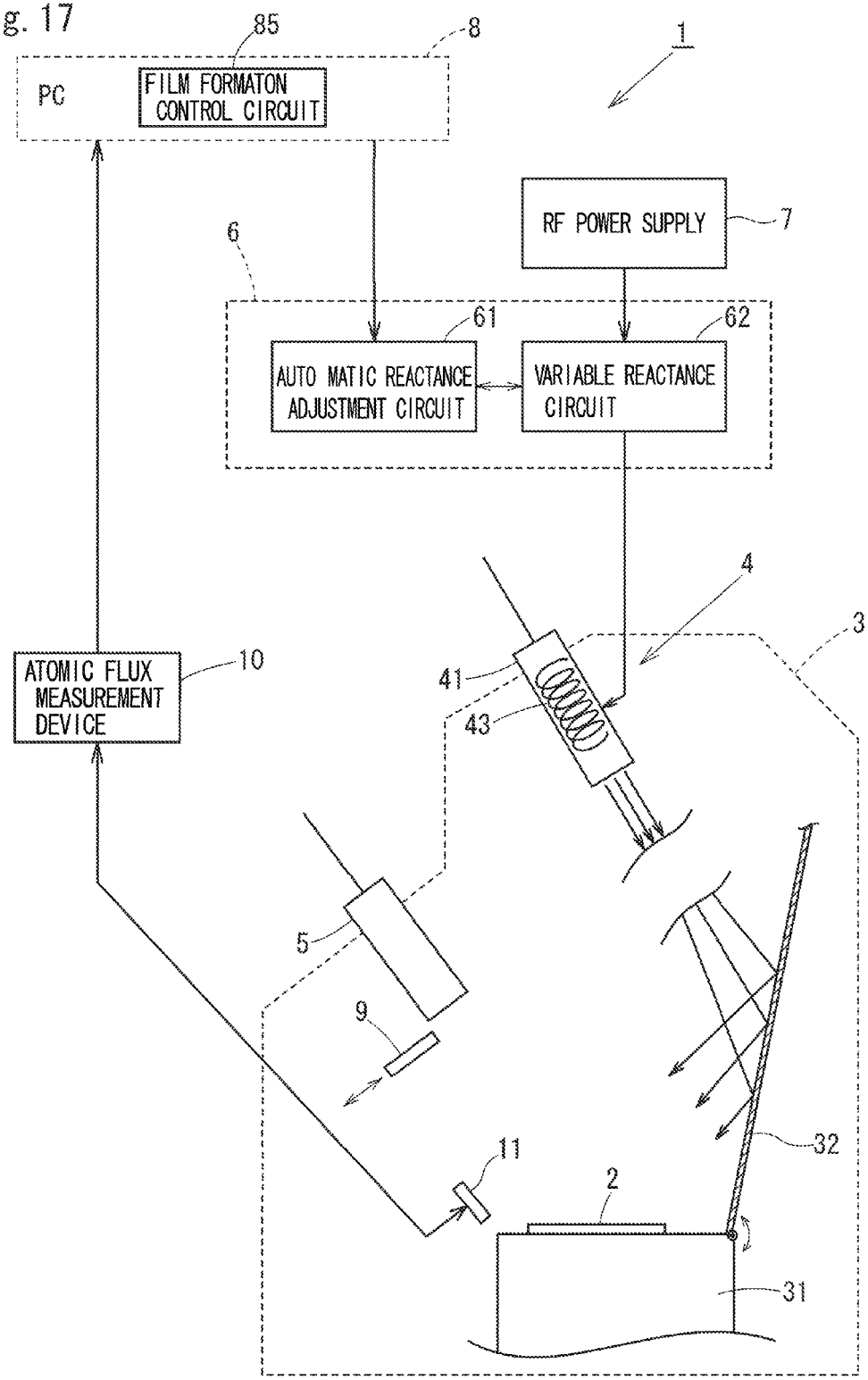
FIG. 17 is a diagram schematically showing a configuration of an MBE growth equipment.
Figure 18:
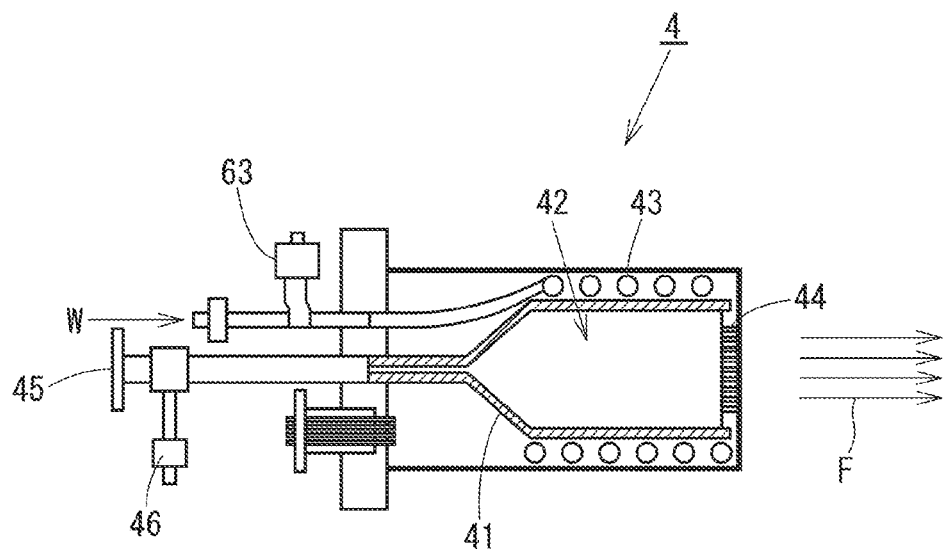
FIG. 18 is a cross-sectional view of the RF excitation cell 4 of FIG. 17.
Figure 19:
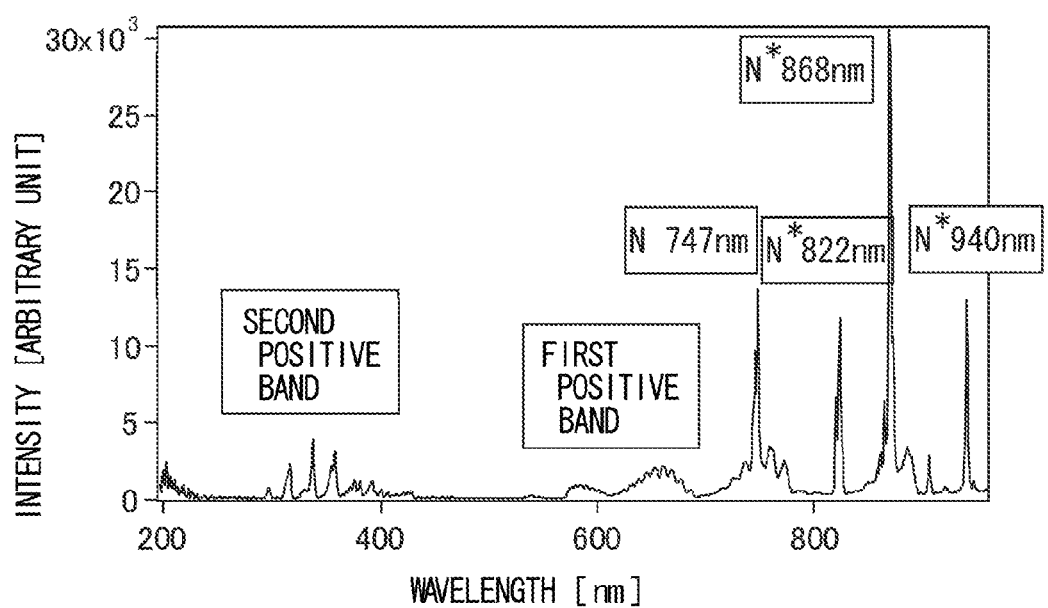
FIG. 19 is a diagram showing a spectrum of a dissociated nitrogen atomic flux emitted from the RF excitation cell 4.

As shown in FIG. 17 described above, the counter electrode body 11a is provided in the vacuum chamber 3 of the MBE growth equipment 1. The flow of the HB-discharge-mode plasma, i.e., active species including excited molecules $N_2$* and dissociated nitrogen atoms (excited atoms N* and ground-state atoms N), which is emitted from the RF excitation cell 4 of the MBE growth equipment 1, repeatedly strikes and rebounds off the shroud, the reflection plate 32 and the like in the vacuum chamber 3 before entering the space portion between the first and second sheet-like electrodes 12 and 13 of the counter electrode body 11a from openings around the space.

As shown in FIG. 3(a), the dissociated nitrogen atoms that have entered the space portion of the counter electrode body 11a are attached to the inner surfaces of the pair of the sheet-like electrodes 12 and 13, with a density distribution corresponding to thermal equilibrium vapor pressure of the space portion. As described above, the atomic current $I_A$ measured by the first direct-current ammeter 16 corresponds to the density distribution of the dissociated nitrogen atoms in the local space in which the counter electrode body 11a is provided, i.e., the amount of flux. Therefore, the amount of the atomic flux can be determined by measuring the value of the atomic current flowing in the counter electrode body 11a.

<Results of Measurement>

Figure 4:
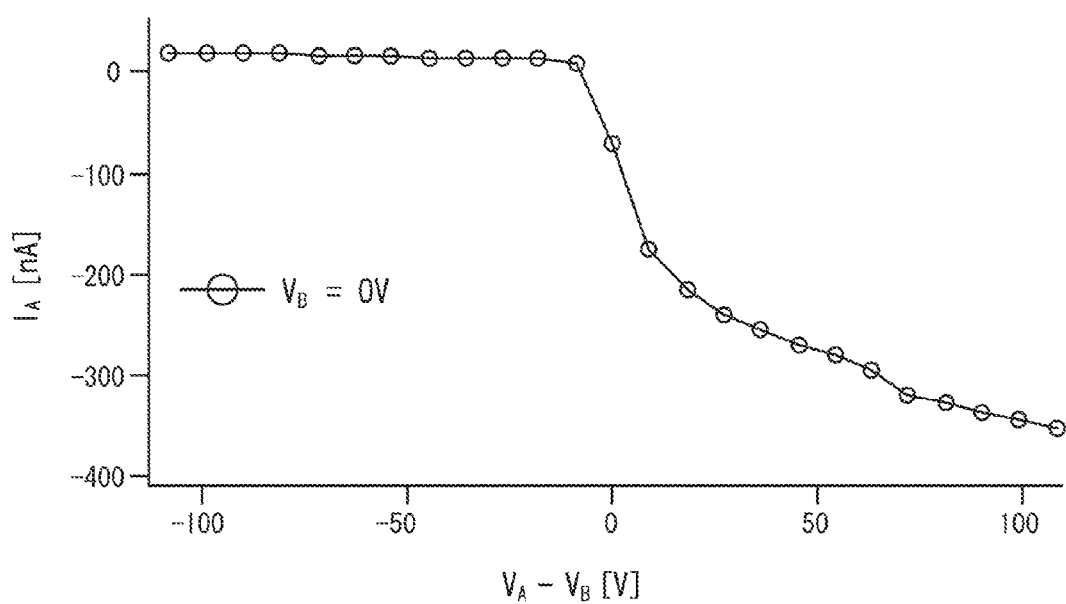
FIG. 4 is a graph of voltage-current characteristics produced based on the result of measurement performed by the atomic flux measurement device of the first embodiment.
Figure 5:
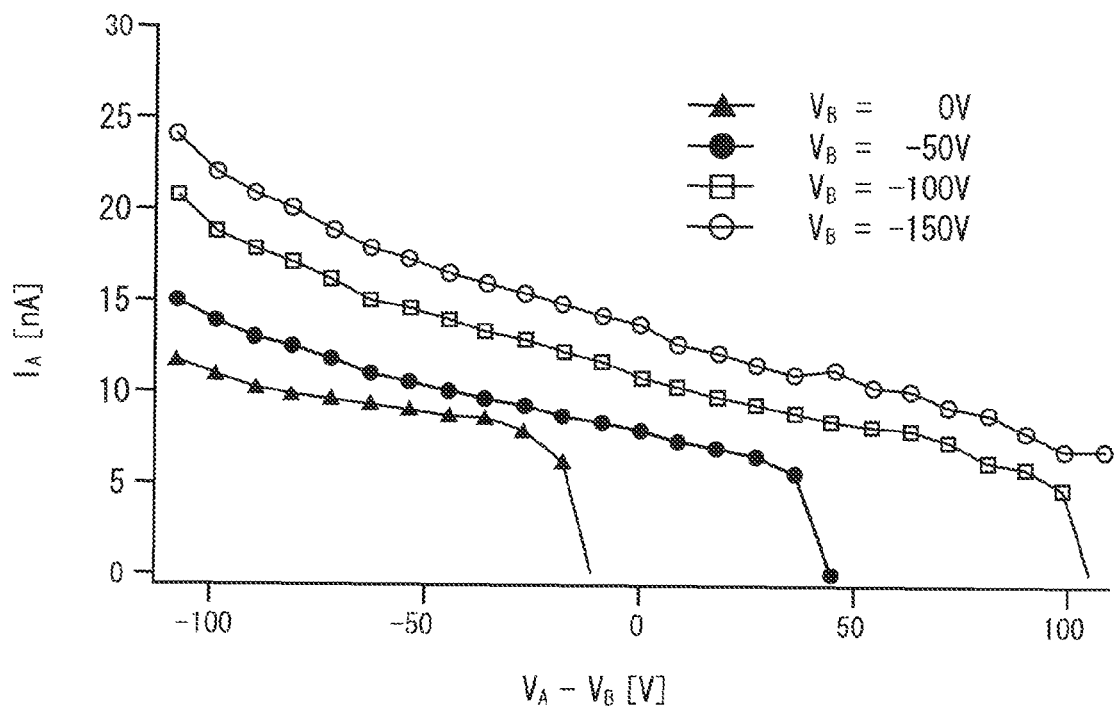
FIG. 5 is a graph of voltage-current characteristics produced based on the result of measurement performed by the atomic flux measurement device of the first embodiment.
Figure 6:
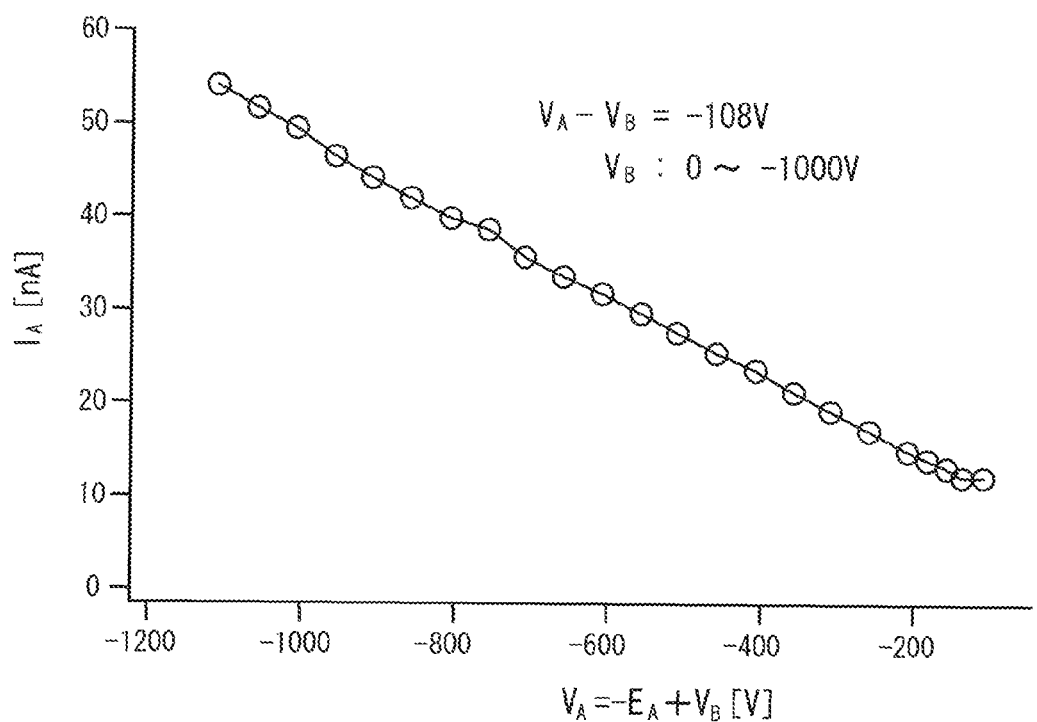
FIG. 6 is a graph of voltage-current characteristics produced based on the result of measurement performed by the atomic flux measurement device of the first embodiment.

The results of measurement of current-voltage characteristics using, the above atomic flux measurement device 10 are shown in FIGS. 4 to 6. FIG. 4 shows a relationship between a potential difference $(V_A-V_B=-E_A)$ [horizontal axis] applied between the first and second sheet-like electrodes 12 and 13 and the atomic current $I_A$ [vertical axis] measured by the first direct-current ammeter 16, where the potential $V_B$ of the second terminal 18 is zero.

According to the measurement result of Fla 4, the atomic current $I_A$ is detected only when the potential $V_A$ $(=-E_A+V_B)$ applied to the first sheet-like electrode 12 has a negative value. Because $V_B$ is set to zero, the negative portion of the potential difference $(V_A-V_B)$ is the atomic current. As the absolute value of the potential $V_A$ increases, the atomic current $I_A$ linearly increases, and changes in the increase of the current are small.

In FIG. 4, if the potential difference $(V_A-V_B=-E_A)$ is positive, a current of electrons contained in the atomic flux around the counter electrode body 11a flows through the first direct-current ammeter 16, but this current has nothing to do with the atomic current.

FIG. 5 shows changes in the atomic current $I_A$ [vertical axis] that occur when the potential $V_B$ of the second terminal 19 is changed to 0, −50 V, −100 V and −150 V and is maintained at the values, and the potential difference $(V_A-V_B=-E_A)$ [horizontal axis] applied between the first and second sheet-like electrodes 12 and 13 is changed. As shown in the upper right portion of the graph, measured values are indicated by different symbols for the different values of the potential $V_B$.

In the four measurement results ($V_B$=0, −50 V, −100 V and −150 V) shown in FIG. 5, their linear portions are not parallel to each other, and their slopes increase as the absolute value of the potential difference $(V_A-V_B=-E_A)$ increases. If the graph is redrawn where the potential difference $(V_A-V_B=-E_A)$ applied between the first and second sheet-like electrodes 12 and 13 is constant, it can be seen that the atomic current $I_A$ changes substantially linearly, depending on the magnitude of the potential $V_A$ of the first direct-current power supply 13.

FIG. 6 shows the result of measurement of current-voltage characteristics that is obtained when the potential difference $(V_A-V_B=-E_A)$ applied between the first and second sheet-like electrodes 12 and 13 is fixed to −108 V and the potential $V_B$ of the second terminal 19 is changed up to −1000 V. It can be seen from this measurement result that the atomic current $I_A$ linearly decreases depending on an increase (a decrease in the absolute value) in the potential $V_A$ of the first terminal 18.

From the three measurement results of FIGS. 4 to 6, it is confirmed that the amount of dissociated nitrogen atoms (N and N*) flux emitted from the RF excitation cell 4 with which the surface of the substrate 2 is indirectly irradiated, i.e., dissociated nitrogen atoms that are emitted from the RF excitation cell 4 and thereafter strike and rebound off the shroud and the like of the vacuum chamber 3 before striking the surface of the substrate 2, can be sufficiently measured. Note that the amount of dissociated nitrogen atoms (N and N*) flux that strike the substrate 2 varies depending on the operation conditions of the RF excitation cell 4, specifically, the high-frequency power applied to the excitation coil 43 of the RF excitation cell 4, the vapor pressure of the active species in the vacuum chamber 3 of the MBE growth equipment 1, the temperature of the shroud of the vacuum chamber 3, and the like.

Incidentally, if the plasma emitted from the RF excitation cell 4 contains charged particles, such as, for example, nitrogen molecule ions $N_2^+$, nitrogen atom ions $N^+$ or electrons $e^-$, a current $I_B$ flowing from the second sheet-like electrode 13 toward the ground terminal 20 is measured by the second direct-current ammeter 17. As described above, the atomic current corresponds to the number of neutral dissociated nitrogen atoms attached to the inner surface of the first sheet-like electrode 12. The current $I_B$ measured by the second direct-current ammeter 17 includes a current of charged particles contained in the plasma and, in addition, an atomic current of neutral dissociated nitrogen atoms attached to the outer surface of the second sheet-like electrode 13. In this case, the current of the charged particles is also included in the current $I_A$ measured by the first direct-current ammeter 16, resulting in an error during measurement of the amount of flux. Therefore, the presence of an error in the atomic current can be detected based on the current $I_B$ of the second direct-current ammeter 17.

<Configuration of Measurement Device>

Referring back to FIG. 1, the current $I_A$ detected by the first direct-current ammeter 16 is converted into digital data by the A/D converter 21 before being input to the PC 8. The PC 8 functions as a controller 81 and a calculator 82 of the atomic flux measurement device 10 in addition to the aforementioned growth control circuit 85. These functions are achieved by reading software stored in the memory 83 and executing the software using a CPU. The digital data that has been input to the PC 8 and stored in the memory 83 is displayed on a display 84 by a control performed by the controller 81. An operator can find out the value of the atomic current in situ.

In this embodiment, the amount of the atomic flux striking the substrate 2 is monitored based on the atomic current flowing through the counter electrode body 11a. If you wish to directly find out the amount of the atomic flux, it is necessary to convert the value of the atomic current into the amount of flux. In this case, it is necessary to prepare a table containing the amount of atomic flux and atomic current values measured under the same conditions, based on which the value of an atomic current is converted into the amount of an atomic flux, and store the table in the memory 83 in advance. If the calculator 82 converts a current value measured by the counter electrode body 11a into the amount of an atomic flux based on the table, and the value of the amount of an atomic flux is displayed on the display 84, the amount of dissociated nitrogen atoms (N and N*) flux can be known in situ.

Additionally, a graph is produced that indicates a correlation relationship between the growth rate of the monocrystalline $Si_3N_4$ buffer layer that is formed on the substrate 2 using the above MBE growth equipment 1 and the value of the atomic current measured by the counter electrode body 11a. If the data of the produced graph is stored as a table in the memory in the growth control circuit 85 (see FIG. 17), the growth control circuit 85 can control the growth rate of the monocrystalline $Si_3N_4$ buffer layer using the data of the table based on the value of the atomic current measured by the counter electrode body 11a.

Similar to the first direct-current ammeter 16, the current value detected by the second direct-current ammeter 17 is converted into digital data by the A/D converter 22 before being input to the PC 8. Note that, in addition to the above control, the controller 81 sets the voltages of the first and second direct-current power supplies 14 and 15 and controls ON/OFF of the first and second direct-current ammeters 16 and 17.

<Procedure of Measurement of Atomic Flux>

Next, a procedure of measuring the amount of dissociated nitrogen atomic flux that strike the substrate 2 using the atomic flux measurement device 10 of this embodiment will be described.

The RF excitation cell 4 is mounted in the cell port of the above MBE growth equipment 1 shown in FIG. 17, while the silicon substrate 2 is fixed to the substrate holder 31 in the vacuum chamber 3. The buffer layer of monocrystalline $Si_3N_4$ is grown on the silicon substrate 2. In this case, a high-frequency power of 500 W is applied to the RF excitation cell 4 so that the RF excitation cell 4 is operated in the HB discharge mode.

As described above, when the monocrystalline $Si_3N_4$ buffer layer is grown on the silicon substrate 2, the substrate 2 is preferably indirectly irradiated with a flux of dissociated nitrogen atoms (ground-state atoms N and dissociated nitrogen atoms N*) emitted from the RF excitation cell 4. The indirect irradiation is achieved by any of the following methods.

A first method is to close the travel direction of the flux of dissociated nitrogen atoms emitted from the RF excitation cell 4 using a shutter (not shown). With this method, dissociated nitrogen atoms emitted from an orifice 44 of the RF excitation cell 4 repeatedly strike and rebound off the shutter and the inner wall of the growth chamber (vacuum chamber), and thereafter, a flux having low energy leaks from a gap at the periphery of the shutter, so that the surface of the substrate 2 is irradiated with the low-energy flux.

A second method is to open the above shutter to irradiate the substrate 2 with a flux of dissociated nitrogen atoms that has been emitted from the RF excitation cell 4 and has repeatedly struck and rebounded off the reflection plate 32 and the shroud provided in the vacuum chamber 3.

The counter electrode body 11 of the atomic flux measurement device 10 is provided in a portion adjacent to the substrate holder 31 at a position that is located away from a region (straight line) connecting the orifice 44 of the RF excitation cell 4 and the surface of the substrate 2. As described above, dissociated nitrogen atoms emitted from the RF excitation cell 2 repeatedly strike and rebound off the shutter (not shown), the reflection plate 32, the shroud and the like provided in front of the RF excitation cell 2 before entering the space portion of the counter electrode body 11a of the atomic flux measurement device 10. Thereafter, the dissociated nitrogen atoms are attached to the surfaces of the sheet-like electrodes 12 and 13 at a density corresponding, to thermal equilibrium vapor pressure of the space portion, so that an atomic current occurs between the electrodes. The atomic current measured by the atomic flux measurement device 10 is sent to the growth control circuit 85, and is used as data for controlling the thickness of the buffer layer.

Figure 7:
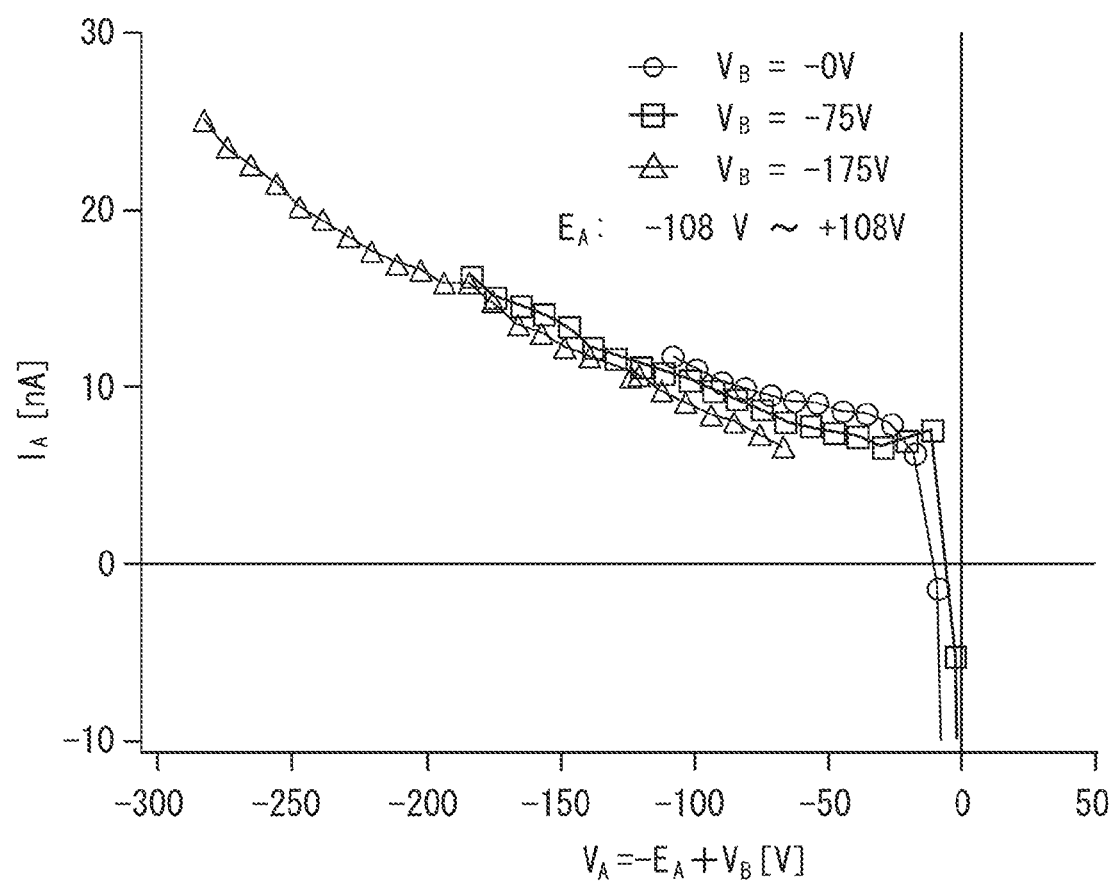
FIG. 7 is a graph of voltage-current characteristics produced based on the result of measurement performed by the atomic flux measurement device of the first embodiment.

In this embodiment, the atomic flux measurement device 10 was used to measure the value of the atomic current while the RF excitation cell 4 was operated under the following conditions. A relationship between the atomic current $I_A$ measured with the first direct-current ammeter 16 and the potential $V_A$ of the first sheet-like electrode 12 at that time is shown in FIGS. 7 to 9.

(1) Power applied to the discharge coil 43 of the RF excitation cell 4: 500 W (2) Flow rate of nitrogen supplied to the discharge chamber 42 of the RF excitation cell 4: 1.38 sccm (3) Pressure in the RF excitation cell 4: about 100 Pa (4) Degree of vacuum in the vacuum chamber 3: $4 \times 10^{-3}$ Pa A graph of FIG. 7 shows a relationship between the potential $V_A$ ($=-E_A+V_B$) of the first terminal and the atomic current $I_A$ measured by the first direct-current ammeter 16, where the electromotive force $E_A$ of the first direct-current power supply 14 was changed within the range of $-108$ V to $+108$ V while the potential $V_B$ of the second terminal 19 was held at $-175$ V, $-75$ V and $0$ V.

It was found that the atomic current $I_A$ varies linearly, depending on the change in the potential $V_A$. From this result, it was found that there is a linear correlation relationship between the measured value of the atomic current $I_A$ and the amount of dissociated nitrogen atoms (N*+N) flux existing in the space portion of the counter electrode body 11a.

The graph of FIG. 8 shows four curves. A first curve indicated by the symbol "○" shows a relationship between the potential $V_A$ ($=-E_A+V_B$) of the first terminal 18 and the atomic current $I_4$ measured by the first direct-current ammeter 16, where the potential $V_B$ of the second terminal 19 was changed within the range of $-800$ V to $0$ V while the electromotive force $E_A$ of the first direct-current power supply 14 was held constant ($-108$ V).

A second curve indicated by the symbol "+" shows a relationship between the potential $V_A$ of the first terminal and the atomic current $I_A$ measured by the first direct-current ammeter 16, where the electromotive force $E_A$ of the first direct-current power supply 16 was changed within the range of $-108$ V to $+108$ V while the potential $V_B$ of the second terminal 19 was held constant (200 V). A third curve indicated by the symbol "▲" shows a relationship between the potential $V_A$ of the first terminal and the atomic current $I_A$ measured by the first direct-current ammeter 16 where the electromotive force $E_A$ of the first direct-current power supply 16 was changed within the range of $-108$ V to $+108$ V while the potential $V_B$ of the second terminal 19 was held constant ($0$ V).

From these measurement results, it was found that the atomic current $I_A$ varies linearly, depending on the magnitude of the electromotive force $E_A$ of the first direct-current power supply 14. Note that a fourth curve indicated by the symbol "◇," which is for reference, shows a relationship between the potential $V_A$ of the first terminal and the current $I_A$ (i.e., a dark current) measured by the first direct-current ammeter 16, where power is not supplied to the RF excitation cell 4.

The graph of FIG. 9 shows a relationship between the potential $V_A$ of the first terminal and the atomic current $I_A$ measured by the first direct-current ammeter 16, where two counter electrode bodies 11a having different spacings D (6 mm and 20 mm) between the pair of the sheet-like electrodes 12 and 13 were used. The counter electrode body having the larger spacing D indicated by the symbol "○" has a larger value of the atomic current $I_A$ than that of the counter electrode body having the smaller spacing D indicated by the symbol "●." This may be because, for the larger spacing D, there is a larger amount of dissociated nitrogen atoms (N*+N) flux in the space portion of the counter electrode body 11a.

Second Embodiment

Figure 10:
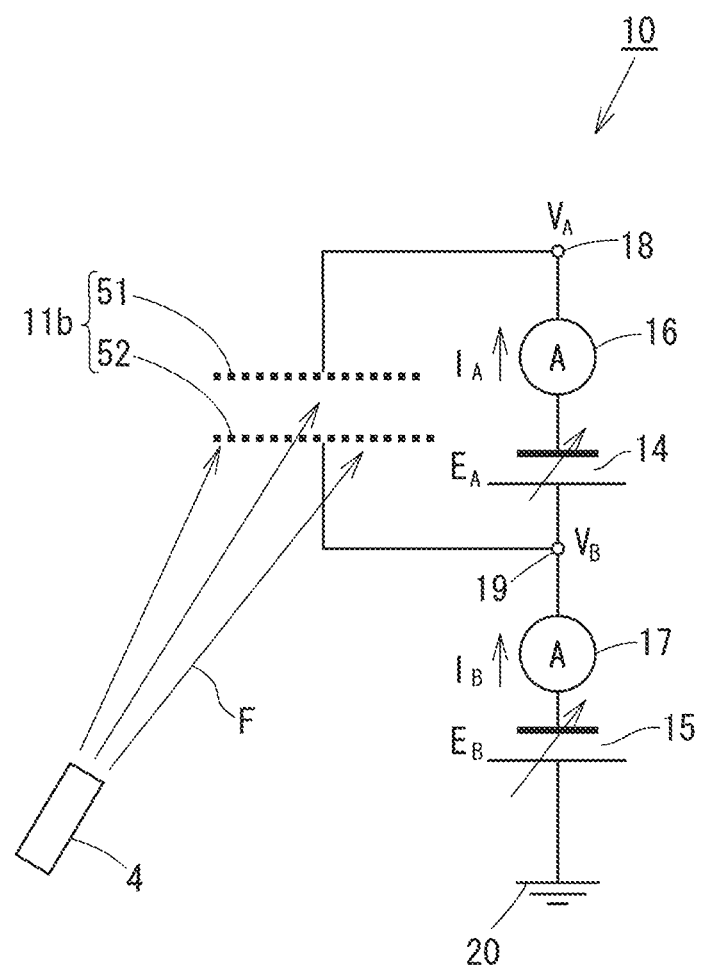
FIG. 10 is a diagram showing a basic configuration of an atomic flux measurement device according to a second embodiment of the present invention.

FIG. 10 shows a basic configuration of an atomic flux measurement device according to a second embodiment of the present invention. In FIG. 10, components having the same functions as those of the atomic flux measurement device of the first embodiment of FIG. 1 are indicated by the same reference characters and will not be described. FIG. 10 additionally shows the RF excitation cell 4 in order to describe the function of the electrode. On the other hand, FIG. 10 does not show the A/D converters 21 and 22 or the PC 8, which will not be described.

<Configuration of Measurement Device>

The atomic flux measurement device of this embodiment is the same as that of the first embodiment, except for the configuration of the counter electrode body. A counter electrode body 11b of this embodiment employs two sheet-like electrodes 51 and 52 formed of a metal mesh sheet (hereinafter referred to as "mesh electrodes") instead of the sheet-like electrodes 12 and 13 of the counter electrode body 11a of the first embodiment.

A reason why the mesh electrode is used as the sheet-like electrode will be described. The counter electrode body 11a of the first embodiment does not have a problem when the amount of dissociated nitrogen atomic flux in indirect irradiation is measured. However, the electrode is harmed of a sheet-like metal, and therefore, when the amount of dissociated nitrogen atomic flux that are emitted from the RF excitation cell 4 and directly strike the substrate 2 (direct irradiation) is measured, the amount of the flux entering the space portion of the counter electrode body varies significantly, depending on the orientation of the electrode. Also, most of the dissociated nitrogen atoms rebound off the surface of the sheet-like electrode to go away from the counter electrode body, and therefore, only a small number of dissociated nitrogen atoms enter the space portion of the counter electrode body 11a to contribute to the atomic current. As a result, the amount of dissociated nitrogen atomic flux cannot be accurately measured.

In contrast to this, when the mesh electrode is used as the sheet-like electrode, a flux F of dissociated nitrogen atoms emitted from the RF excitation cell 4 passes through interstices of the mesh electrode to enter the space portion of the counter electrode body 11b, so that the thermal equilibrium vapor pressure of the space portion increases. The dissociated nitrogen atoms are attached to the electrode surface at a density corresponding to thermal equilibrium vapor pressure, resulting in an atomic current.

As in the first embodiment, the first and second direct-current power supplies 14 and 15 apply a negative bias potential $V_A = -E_A + V_B$ to the first mesh electrode 51. An atomic current $I_A$ based on self-ionization of the dissociated nitrogen atoms (N*+N) attached to the inner surface of the mesh electrode 51 flows between the mesh electrodes 51 and 52.

Thus, the counter electrode body 11b can measure not only the amount of a flux of dissociated nitrogen atoms (N*+N) that are emitted from the RF excitation cell 4 and enter through peripheral openings of the mesh electrodes 51 and 52 (indirect irradiation), but also the amount of a flux of dissociated nitrogen atoms (N*+N) that are emitted from the RF excitation cell 4 and pass through the interstices of the mesh electrode 52 to enter the space portion of the counter electrode body 11b (direct irradiation).

<Specific Configuration of Counter Electrode Body>

FIG. 11 shows an example specific configuration of the counter electrode body 11b. The counter electrode body 11b includes two metal mesh sheets having different lengths that are rolled, facing each other with a spacing between them. If the counter electrode body 11b thus includes the mesh electrodes robed into a spiral, the surface areas of the mesh electrodes 51 and 52 can be increased without an increase in the volume of the counter electrode body. As a result, the amount of a flux attached to the inner surface of the mesh electrode 51 increases, and therefore, the value of the atomic current proportionately increases, whereby the sensitivity of current measurement can be increased, and therefore, the accuracy of detection of the amount flux can be increased.

In this embodiment, the mesh electrode 51 was formed of a mesh (#100 (No. 100)) of stainless steel (SUS404) and had a size of 140 mm (W)×300 mm (L), and the mesh electrode 52 was formed of a mesh (#100 (No. 100)) of stainless steel (SUS404) and had a size of 140 mm (W)×250 mm (L). The mesh electrodes 51 and 52 are robed, facing each other with a plurality of alumina bushings (insulating spacers) 53 with a diameter of 6 mm being interposed between them to form a spacing (D) of 6 mm.

Figure 11A:
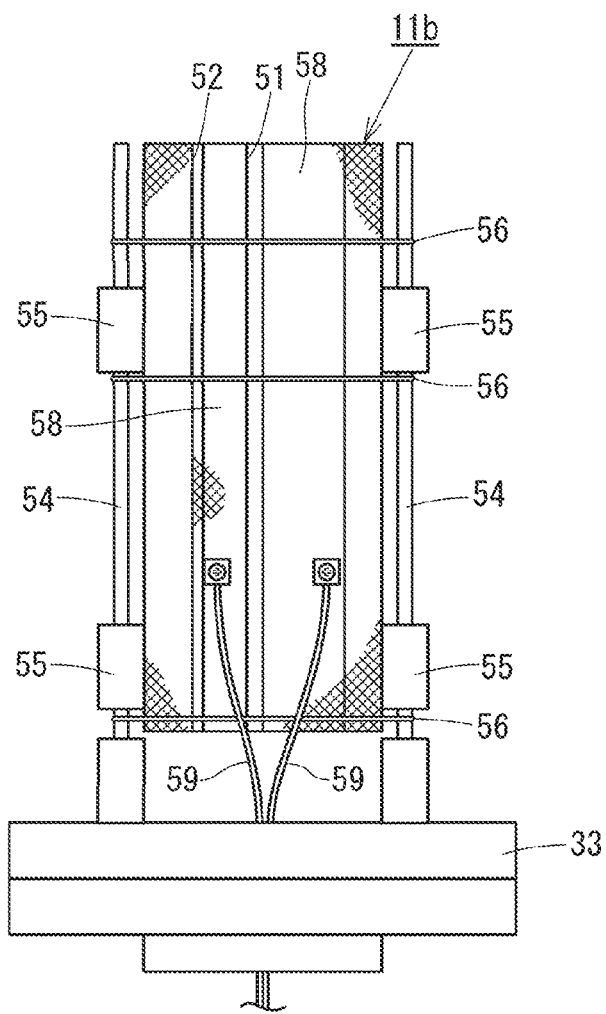
FIGS. 11(a) and 11(b) are diagrams showing an example specific configuration of a counter electrode body in the second embodiment.
Figure 11B:
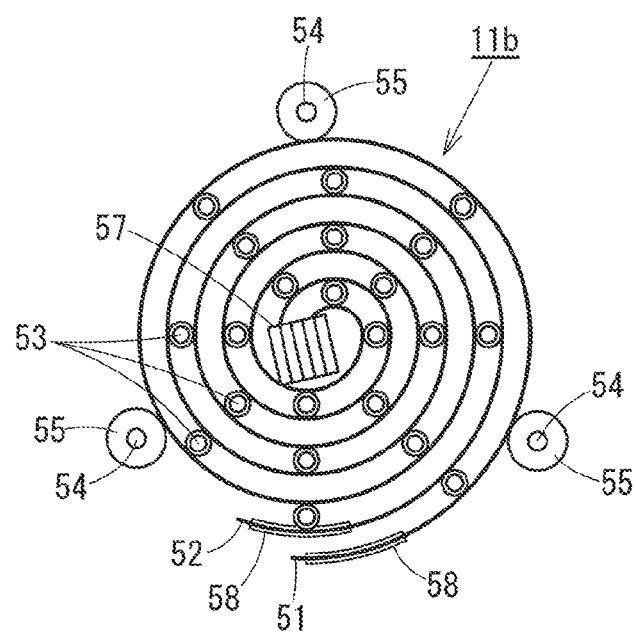

As shown in FIGS. 11(a) and 11(b), three support posts 54 of aluminum are provided to stand on a flange 33 of the cell shutter. The two mesh electrodes 51 and 52 rolled into a spiral are inserted in the space portion formed by the three support posts 54. An alumina tube 55 for insulation is mounted around each support post 54. The spiral mesh electrodes 51 and 52 are fixed to the three support posts 54 by wrapping a fixing, band 56 of a heat-resistant insulating material around the outer circumference of the three support posts 54. Moreover, innermost end portions of the mesh electrodes 5 and 52 are immobilized by an insulating fixing device 57 while they are separated from each other by the spacing D. The outermost end portions of the mesh electrodes 51 and 52 are electrically insulated via sheet-like separators 58 of mica. The mesh electrodes 51 and 52 are connected to the terminals 18 and 19, respectively, via wires 59.

In the counter electrode body 11b of this embodiment, the mesh electrode bodies 51 and 52 are rolled into a spiral, whereby the electrode area is increased without an increase in the volume, and therefore, the amount of dissociated nitrogen atoms attached to the mesh electrode can be increased. As a result, the sensitivity of measurement of the atomic current can be increased, and therefore, the accuracy of detection of the amount of the atomic flux can be increased.

Third Embodiment

Figure 12:
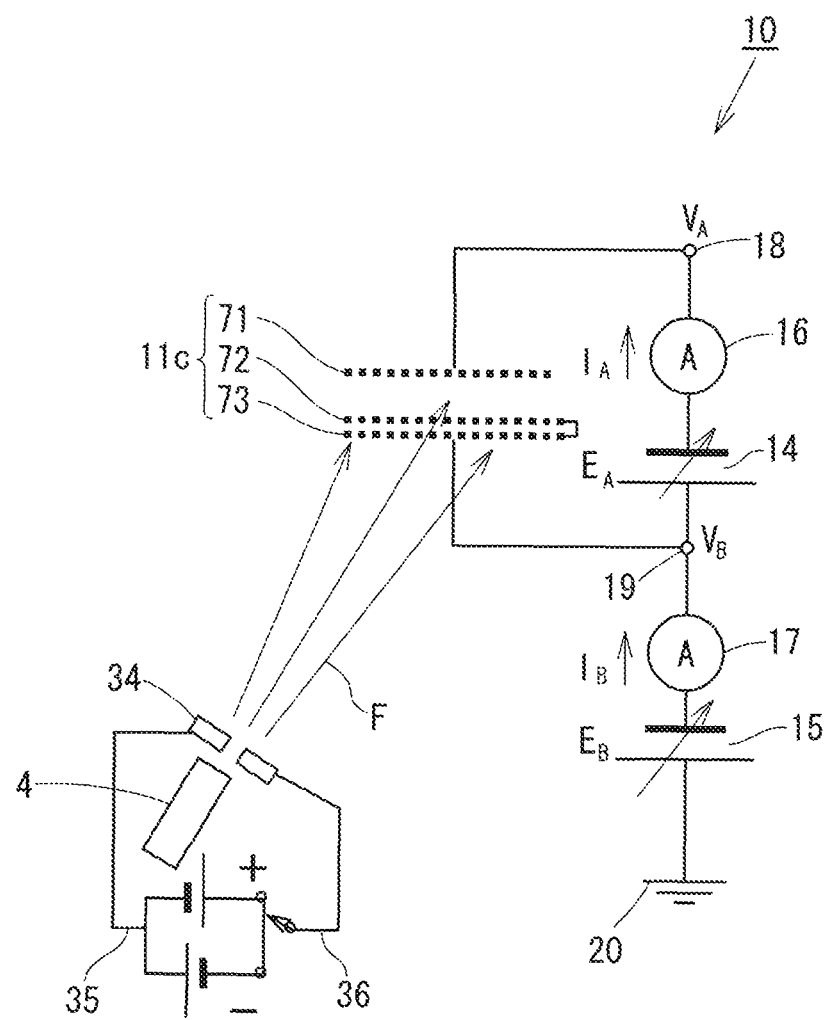
FIG. 12 is a diagram showing a basic configuration of an atomic flux measurement device according to a third embodiment of the present invention.

FIG. 12 shows a basic configuration of an atomic flux measurement device according to a third embodiment of the present invention. In FIG. 12, components having the same functions as those of the atomic flux measurement device s of the first and second embodiments are indicated by the same reference characters and will not be described. As in FIG. 10, FIG. 12 additionally shows the RF excitation cell 4 in order to describe the function of the electrode. On the other hand, FIG. 12 does not show the A/D converters 21 and 22 or the PC 8, which will not be described.

<Configuration of Measurement Device>

As with the counter electrode body 11b of the second embodiment, a counter electrode body 11c of this embodiment employs two mesh electrodes 71 and 72 formed of a metal mesh sheet. On the other hand, unlike the counter electrode body 11b of the second embodiment, the counter electrode body 11c includes a third mesh electrode 73 formed of a metal mesh sheet that is provided on the outer side of the second mesh electrode 72 with a predetermined spacing between them.

If the third mesh electrode 73 is held at an appropriate potential (e.g., the same potential as that of the mesh electrode 72), charged particles $N_2^+$, $e^-$ and the like contained in a flux F can be prevented from entering the mesh electrodes 71 and 72 to some extent. In other words, the mesh electrode 73 functions as a filter that prevents a noise or error current from being added to an atomic current flowing through a closed circuit including the mesh electrodes 71 and 72.

Note that although not essential to the atomic flux measurement device of the present invention, as shown in FIG. 12, a pair of eliminator electrodes 34 may be provided in the vicinity of a plasma outlet of the RF excitation cell 4 so that charged particles contained in a plasma flux are laterally deviated, whereby charged particles can be prevented from being contained in the flux F entering the atomic flux measurement device 10.

The eliminator electrode pair 34 includes a pair of electromagnets facing each other to generate a static magnetic field intersecting the plasma flux emitted from the RF excitation cell 4, thereby laterally deviating the charged particles contained in the plasma flux.

The eliminator electrode pair 34 prevents charged particles from being contained in the flux F emitted from the RF excitation cell 4 to the counter electrode body 11c. Therefore, measurement error in an atomic current in the atomic flux measurement device can be reduced. Note that, in FIG. 12, a direct-current power supply 35 is designed so that the polarity of the potential that is applied to the eliminator electrode pair 34 can be changed using a switch 36.

<Specific Configuration of Counter Electrode Body>

Figure 13:
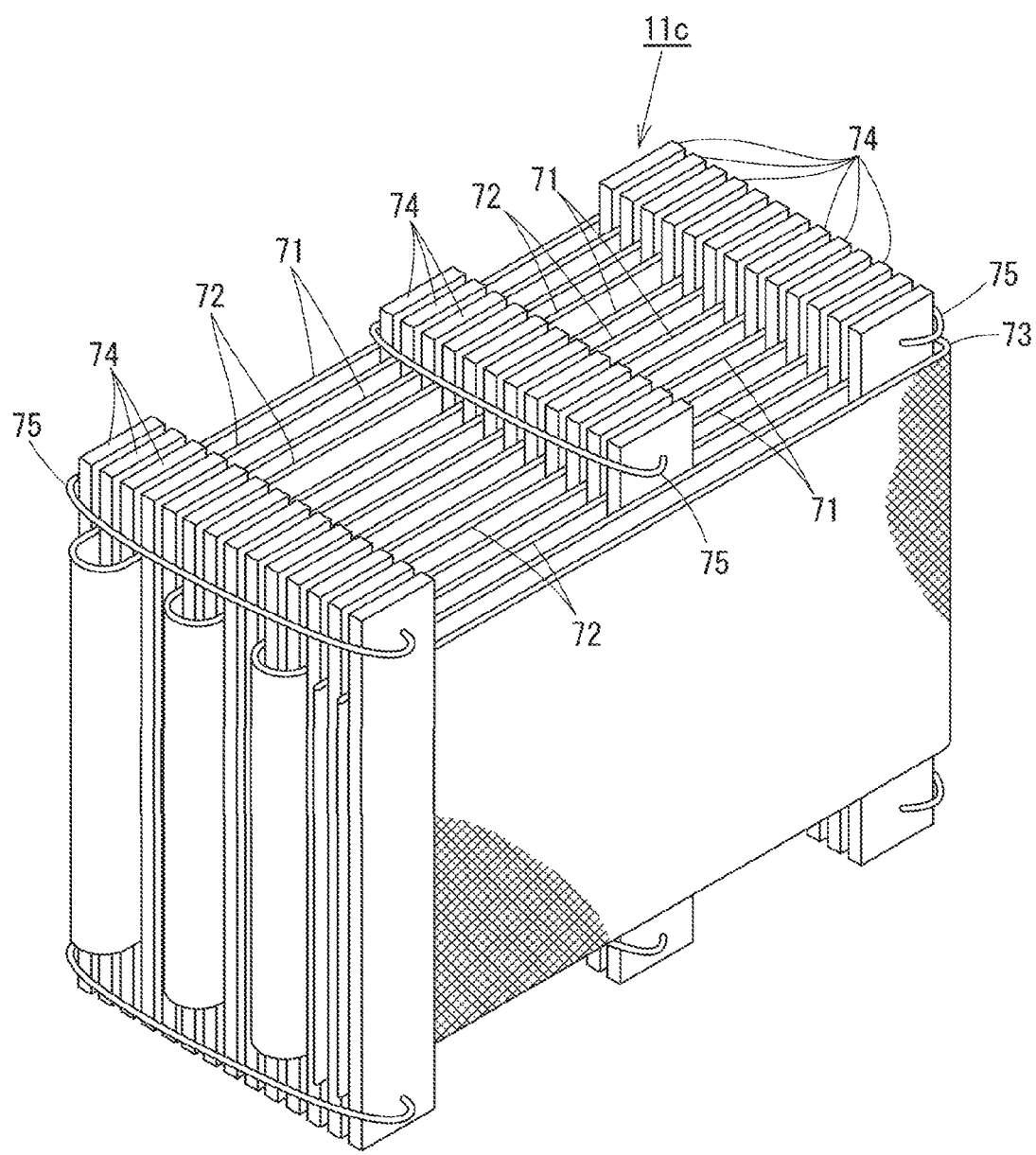
FIG. 13 is a perspective view showing an example of a specific configuration of a counter electrode body in the third embodiment.
Figure 14:
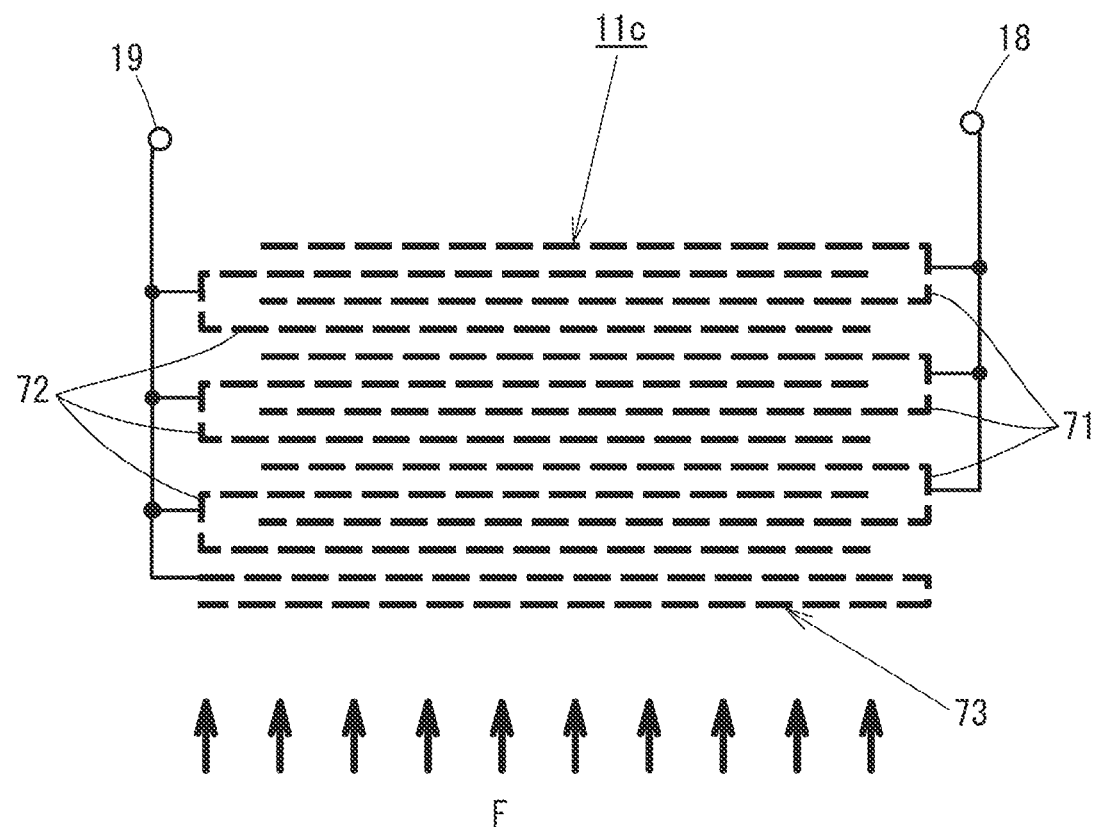
FIG. 14 is a diagram schematically showing a circuit of the counter electrode body in the third embodiment.

FIG. 13 shows an example specific configuration of the counter electrode body 11c of this embodiment. FIG. 14 shows a schematic circuit diagram of the counter electrode body 11c shown in FIG. 13. The counter electrode body 11c of FIG. 13 is different from the counter electrode body 11b of the second embodiment shown in FIG. 11 in two ways. A first difference will be described hereinafter.

In the counter electrode body 11b, the two mesh electrodes 51 and 52 having large areas are rolled to form a counter electrode body, in contrast to this, the counter electrode body 11c includes a plurality of the plate-like mesh electrodes 71 and 72, which face each other and are alternately arranged with a spacing.

In the counter electrode body 11c, the first mesh electrodes 71 including plate-like metal mesh sheets are joined together in the shape of a comb, and the second mesh electrodes 72 having a similar configuration, are alternately arranged and combined with a ceramic insulating spacer 74 being interposed between each electrode. Note that the insulating spacers 74 are fastened together using a wire 75 so that the insulating spacers 74 are not displaced.

The flux F of dissociated nitrogen atoms emitted from the RF excitation cell 4 enters a space portion between each electrode not only from a peripheral portion (indirect irradiation) but also from the front sides of the mesh electrodes 72 (direct irradiation). The dissociated nitrogen atoms (N and N*) coming to the space portions are attached to the inner surfaces of the first mesh electrodes 71, so that an atomic current flows between both electrodes.

While the size of the counter electrode body 11b is reduced by rolling the mesh electrodes, the size of the counter electrode body 11c is reduced by stacking the mesh electrodes. By using a plurality of the mesh electrodes 71 and 72 that are put on top of each other, the mesh electrode area is increased without an increase in the volume of the counter electrode body, whereby the amount of dissociated nitrogen atoms attached to the electrode surface is increased. As a result, the sensitivity of measurement of the atomic current can be increased, and therefore, the accuracy of detection of the amount of the dissociated nitrogen atomic flux can be increased.

A second difference is that the comb-like third mesh electrode 73 is provided in front of the counter electrode body. As described above, the mesh electrode 73 has a function of preventing a noise or error current from being added to the atomic current flowing through the closed circuit including the mesh electrodes 71 and 72. As shown in FIG. 14, the mesh electrode 73 substantially, but not entirely, prevents charged particles $N_2^+$, $e^-$ and the like contained in the flux F coming from the front of the counter electrode body from entering the inside of the counter electrode body.

Note that the configuration of the counter electrode body 11c is not limited to that shown in FIG. 13. Although three lines of the spacers 74 are provided in the counter electrode body of FIG. 13, the spacing may be held using any dedicated jig that can maintain insulation between the mesh electrodes.

Fourth Embodiment

Figure 15:
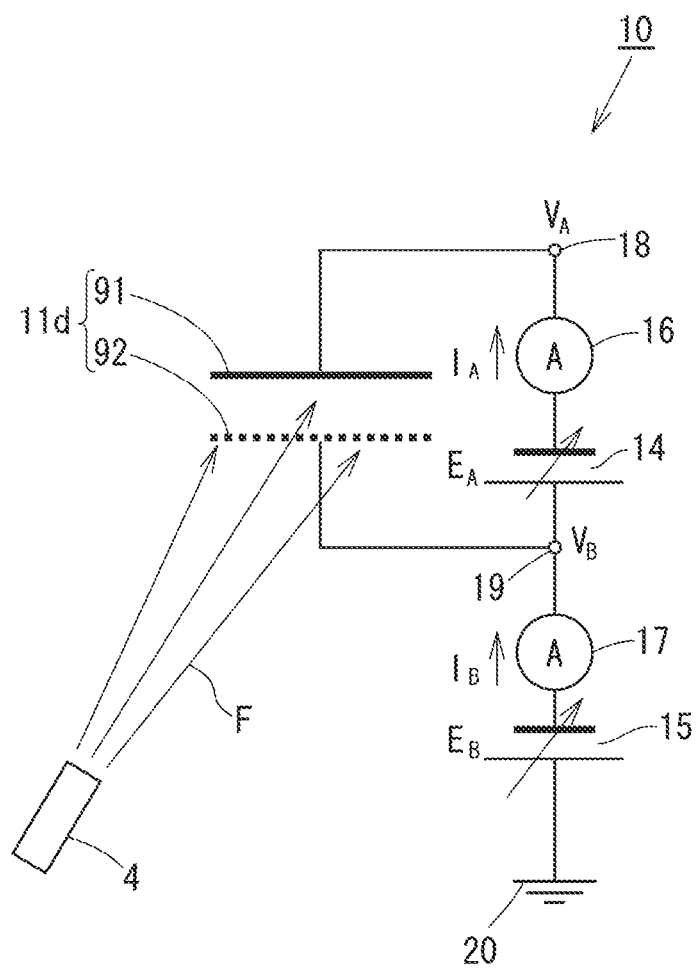
FIG. 15 is a diagram showing a basic configuration of an atomic flux measurement device according to a fourth embodiment of the present invention.

FIG. 15 shows a basic configuration of an atomic flux measurement device according to a fourth embodiment of the present invention. In FIG. 15, components having the same functions as those of the atomic flux measurement device s of the first to third embodiments are indicated by the same reference characters and will not be described. On the other hand, FIG. 15 does not show the A/D converters 21 and 22 or the PC 8, which will not be described.

<Configuration of Measurement Device>

The atomic flux measurement device of this embodiment is the same as those of the first and second embodiments, except for the configuration of the counter electrode body. In a counter electrode body 11d of this embodiment, a sheet-like electrode 91 similar to that of the first embodiment is used as a first sheet-like electrode that is held at a potential $V_A$, and a mesh electrode 92 similar to that of the second embodiment is used as a second sheet-like electrode that is held at a potential $V_B$.

As in the second embodiment, a mesh electrode is used as the second sheet-like electrode 92 to which an atomic flux is input. Therefore, a flux F of dissociated nitrogen atoms emitted from the RF excitation cell 4 passes through interstices of the mesh electrode to enter a space portion of the counter electrode body 11d, so that thermal equilibrium vapor pressure of the space portion increases. The dissociated nitrogen atoms are attached to the electrode surface at a density corresponding to thermal equilibrium vapor pressure, resulting in an atomic current.

On the other hand, because the sheet-like electrode 91 similar to that of the first embodiment is used as the first sheet-like electrode that is held at the potential $V_A$, most of the dissociated nitrogen atoms that have passed through the mesh electrode 92 to enter the space portion of the counter electrode body 11d make contact with a surface of the sheet-like electrode 91. As a result, the value of the atomic current can be expected to increase compared to the counter electrode body 11b of the second embodiment.

<Specific Configuration of Counter Electrode Body>

Figure 16:
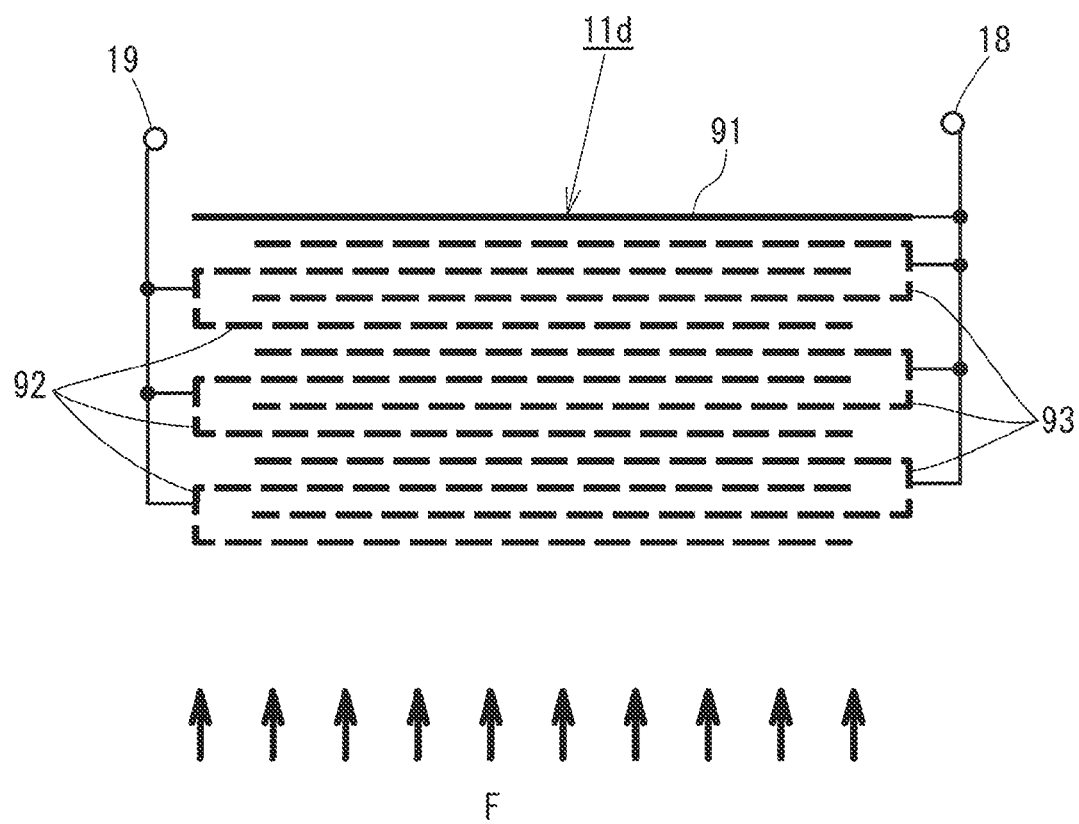
FIG. 16 is a diagram schematically showing a circuit of a counter electrode body in the fourth embodiment.

FIG. 16 schematically shows a circuit diagram of a specific configuration of the counter electrode body 11d of this embodiment. Although not shown, the specific configuration of the counter electrode body 11d is almost the same as that of the counter electrode body 11c of the third embodiment shown in FIG. 13, i.e., first mesh electrodes 93 and second mesh electrodes 92 are alternately stacked.

In the counter electrode body 11d of this embodiment, the first sheet-like electrode that is held at the potential $V_A$ includes the sheet-like electrode 91 and the mesh electrode 93. Specifically, as shown in FIG. 16, the third mesh electrode 73 of the counter electrode body 11c of the third embodiment is removed, and instead, the plate-like sheet-like electrode 91 is provided on the side opposite to the side that an atomic flux enters while being separated from the mesh electrode 93 by a predetermined spacing. Note that the third mesh electrode 73 of the counter electrode body 11c may be left as it is.

As described above, most of the dissociated nitrogen atoms that have passed through interstices of the mesh electrodes 92 and 93 make contact with the surface of the sheet-like electrode 91, and therefore, the value of the atomic current can be expected to increase compared to the counter electrode body 11c of the third embodiment.

As described above, the atomic flux measurement device of the present invention holds the first sheet-like electrode at a negative potential, and further, reduces the value of the potential, thereby increasing the sensitivity of measurement of the atomic current. Therefore, the atomic current can be measured using a relatively low-cost ammeter. As a result, the manufacturing cost of the measurement device can be reduced.

The sheet-like electrodes are formed of a metal mesh sheet, and the sheets are rolled or stacked. As a result, the electrode surface area can be increased without an increase in the volume of the counter electrode body. Therefore, a compact atomic flux measurement device having a high measurement sensitivity can be provided.

Note that, in each of the above embodiments, the atomic flux measurement device 10 is used to monitor the amount of nitrogen active species (N and N*) flux emitted from the RF excitation cell 4. The atomic flux measurement device of the present invention is not limited to this application.

Hydrogen gas $H_2$ or oxygen gas $O_2$ may be supplied to the RF excitation cell 4, and a relatively high degree of high-frequency power may be applied to the excitation coil 43 of the RF excitation cell 4 to operate the RF excitation cell 4 in the HB discharge mode so that to flux of dissociated hydrogen atoms (H* and H) or dissociated oxygen atoms (O* and O) are emitted from the RF excitation cell 4. The flux of dissociated hydrogen atoms or dissociated oxygen atoms that is emitted from the RF excitation cell 4, and thereafter, repeatedly strike and rebound off the shroud, the reflection plate 32 and the like of the vacuum chamber 3, may be caused to enter the counter electrode body 11c. The atomic current may be measured by the atomic flux measurement device 10. As a result, the amount of the dissociated hydrogen atomic or the dissociated oxygen atomic flux may be determined.

The atomic flux measurement device of the present invention is not limited to the growth process on the substrate surface in the vacuum chamber 3 of the MBE growth equipment, and is, of course, applicable to treatments, such as etching or oxidation, in a chamber under vacuum conditions.

The atomic flux measurement device 10 was provided in the shutter port of the nitrogen RF excitation cell 2 of the MBE growth equipment at a position (indirect irradiation position) that is not directly irradiated with a dissociated nitrogen atomic flux from the nitrogen RF excitation cell 4. The silicon substrate 2 fixed to the substrate holder 31 in the vacuum chamber 3 was indirectly irradiated with a flux of dissociated nitrogen atoms from the nitrogen RF excitation cell 4 so that the dissociated nitrogen atoms are allowed to react with Si atoms on the surface of the silicon substrate 2 (i.e., so-called surface/interface reaction). The process of growth of a monocrystalline $Si_3N_4$ buffer layer by the reaction was observed based on the atomic current measured by the atomic flux measurement device 10. As a result, as the amount of dissociated nitrogen atoms that are emitted from the nitrogen RF excitation cell 4 and are attached to the shroud (sidewall portion) increases, the amount of dissociated nitrogen atoms that strike the substrate 2 decreases, and therefore, the growth rate of the monocrystalline $Si_3N_4$ buffer layer decreases.

The undesired decrease in the growth rate due to the increase in the dissociated nitrogen atoms adsorbed to the shroud is overcome as follows. As in an activity control type nitride MBE growth equipment (see JP 2008-78200 A) previously proposed by the present inventors, the discharge modes (the LB discharge mode and the HB discharge mode) of the nitrogen RF excitation cell 4 are alternately switched at appropriate time intervals (duty factor). Atoms of a dissociated nitrogen atomic flux generated during the HB discharge mode period that have been adsorbed to the shroud during one LB discharge mode period are prevented from being deposited on the cooled shroud surface by flushing during the succeeding LB discharge mode period, whereby the decrease in the growth rate of the monocrystalline $Si_3N_4$ buffer layer on the substrate surface can be effectively prevented.

REFERENCE SIGNS LIST

1 MBE GROWTH EQUIPMENT
2 SUBSTRATE
3 VACUUM CHAMBER
4 RF EXCITATION CELL
5 METAL MOLECULAR BEAM CELL
6 RF MATCHING BOX
7 RF POWER SUPPLY
8 PC
9 SHUTTER
10 ATOMIC FLUX MEASUREMENT DEVICE
11a-11d COUNTER ELECTRODE BODY
12, 13, 91, 93 SHEET-LIKE ELECTRODE
14, 15 DIRECT-CURRENT POWER SUPPLY
16, 17 DIRECT-CURRENT AMMETER
18, 19 TERMINAL
20 GROUND TERMINAL 21, 22 A/D CONVERTER
23 SPACER
27, 28, 59, 75 WIRE
29 ALUMINUM INSULATING TUBE
31 SUBSTRATE HOLDER
32 REFLECTION PLATE
51, 52, 71, 72, 73, 92 MESH ELECTRODE
53 ALUMINA BUSHING
54 SUPPORT POST
55 ALUMINA TUBE
56 FIXING BAND
57 FIXING DEVICE
58 SEPARATOR
74 INSULATING SPACER
75 WIRE
81 CONTROLLER
82 CALCULATOR
83 MEMORY
84 DISPLAY

The invention claimed is:

1. An atomic flux measurement device for measuring an amount of disassociated atomic flux that are emitted from a plasma generation cell to a vacuum chamber maintained at a high vacuum, comprising:
 a counter electrode body including a pair of first and second sheet-like electrodes that face each other and are arranged substantially parallel to each other with a predetermined spacing between them;
 a first direct-current power supply configured to apply a direct-current voltage between the first and second sheet-like electrodes to cause the atoms attached to an inner surface of the first sheet-like electrode to undergo self-ionization so that a current flows between the first and second sheet-like electrodes;
 a direct-current ammeter provided between the first and second sheet-like electrodes and configured to measure a value of the current flowing due to the self-ionization of the atoms attached to the inner surface of the first sheet-like electrode; and
 a calculator configured to calculate the amount of disassociated atomic flux based on a table showing a relationship between the value of the current flowing due to the self-ionization of atoms measured by the direct-current ammeter and the amount of disassociated atomic flux emitted to the vacuum chamber,
 wherein the first and second sheet-like electrodes are formed of a plurality of plate-like metal mesh sheets having substantially the same shape,
 wherein the first and second sheet-like electrodes of the counter electrode body are U-shaped and stacked in an interleaved manner with respect to each other with a predetermined spacing.

2. The atomic flux measurement device according to claim 1, wherein the counter electrode body includes a third sheet-like electrode that is formed of a metal mesh sheet and is placed on a side of the counter electrode body where an atomic flux enters, and the potential of the third sheet-like electrode is set to be the same as the potential of the second sheet-like electrode.

3. The atomic flux measurement device according to claim 1, wherein the counter electrode body includes a fourth sheet-like electrode placed outside the first sheet-like electrode, on a side opposite to the side where an atomic flux enters, while being separated from the first sheet-like electrode by a predetermined spacing, and the fourth sheet-like electrode is connected to the first sheet-like electrode.

4. The atomic flux measurement device according to claim 1, further comprising:
 an A/D converter configured to convert the value of the atomic current measured by the direct-current ammeter into digital data;
 a memory configured to store the digital data output from the A/D converter;
 a display configured to display the digital data stored in the memory; and
 a controller configured to write and read data to and from the memory and control operation of the display.

5. The atomic flux measurement device according to claim 4, wherein the calculator is further configured to:
 calculate the amount of flux based on the value of the atomic current measured by the direct-current ammeter,
 wherein:
 read out a table indicating the relationship between values of atomic currents and amount of flux corresponding to the values of the atomic currents, the table being previously stored in the memory, and
 check the value of the atomic current measured by the direct-current ammeter against the values of the atomic currents stored in the memory, to calculate an amount of the flux corresponding to the value of the atomic current measured by the direct-current ammeter.

6. The atomic flux measurement device according to claim 1, wherein the atomic flux is generated by dissociation of any molecule of hydrogen $H_2$, nitrogen $N_2$ or oxygen $O_2$.

* * * * *